(12) United States Patent
Leedman et al.

(10) Patent No.: US 8,673,872 B2
(45) Date of Patent: Mar. 18, 2014

(54) METHOD OF MODULATION OF EXPRESSION OF EPIDERMAL GROWTH FACTOR RECEPTOR(EGFR) INVOLVING MIRNA

(75) Inventors: Peter Leedman, Mt. Claremont (AU); Keith Giles, Mullaloo (AU); Rebecca Jane Webster, Shenton Park (AU)

(73) Assignee: The University of Western Australia, Nedlands, Western Australia (AU)

(*) Notice: Subject to any disclaimer, the term of this patent is extended or adjusted under 35 U.S.C. 154(b) by 147 days.

(21) Appl. No.: 12/310,509

(22) PCT Filed: Aug. 28, 2007

(86) PCT No.: PCT/AU2007/001247
§ 371 (c)(1),
(2), (4) Date: Aug. 25, 2009

(87) PCT Pub. No.: WO2008/025073
PCT Pub. Date: Mar. 6, 2008

(65) Prior Publication Data
US 2010/0016411 A1    Jan. 21, 2010

(30) Foreign Application Priority Data

Aug. 28, 2006   (AU) ................................ 2006904662
Feb. 6, 2007    (AU) ................................ 2007900558

(51) Int. Cl.
*C12N 15/11* (2006.01)

(52) U.S. Cl.
USPC ...................................................... 514/44 A

(58) Field of Classification Search
USPC ...................................................... 514/44 A
See application file for complete search history.

(56) References Cited

U.S. PATENT DOCUMENTS

| | | | |
|---|---|---|---|
| 2004/0121323 A1* | 6/2004 | Leedman et al. | 435/6 |
| 2005/0221354 A1 | 10/2005 | Mounts | 435/6 |
| 2005/0261218 A1* | 11/2005 | Esau et al. | 514/44 |
| 2006/0172311 A1 | 8/2006 | Cohen et al. | 435/6 |
| 2006/0247193 A1* | 11/2006 | Taira et al. | 514/44 |
| 2007/0003575 A1* | 1/2007 | Bentwich et al. | 424/204.1 |
| 2008/0171715 A1* | 7/2008 | Brown et al. | 514/44 |
| 2010/0297615 A1* | 11/2010 | Seshagiri | 435/6 |

FOREIGN PATENT DOCUMENTS

| | | |
|---|---|---|
| WO | WO 02/053774 A2 | 7/2002 |
| WO | WO 02/081492 A1 | 10/2002 |

OTHER PUBLICATIONS

New & Analysis, An audience with . . . Jean-Jaques Garaud, Nature 9: 500, 2010.*
Pei et al. RNA 2010,16: 1-11.*
Cullen Virus Research 102, 2004, 3-9.*
Kefas et al. Cancer Research; 68:3566-3572, 2008.*
Cheng et al. Supplementary material Nucleic Acid Research 2005, 33, pp. 1-2.*
Kefas et al. Cancer Res. 2008:68:3566-3572.*
Database GB MAM, Accession No. DQ64282, Jun. 26, 2006.
Li et al., "A microRNA mediates EGF receptor signaling and promotes photoreceptor differentiation in the *Drosophila* eye", *Cell*, 123:1267-1277 (2005).
Yoo et al., "LIN-12/Notch Activation Leads to MicroRNA-Mediated Down-Regulation of Vav in *C. elegans*", *Science*, 310:1330-1333 (2005).
Cheng et al. "Antisense inhibition of human miRNAs and indications for an involvement of miRNA in cell growth and apoptosis," Nucleic Acids Res. Mar. 1, 2005;33(4):1290-1297.
Esau et al. "miR-122 regulation of lipid metabolism revealed by in vivo antisense targeting," Cell Metabol., 2006, 3:87-98.
Felli et al., "MicroRNAs 221 and 222 inhibit normal erythropoiesis and erythroleukemic cell growth via kit receptor down-modulation," PNAS, 2005, 102(50):18081-18086.
Kwon et al., "MicroRNA1 influences cardiac differentiation in *Drosophila* and regulates Notch signaling," PNAS, 2005, 102(52):18986-18991.
McManus et al., "Gene silencing using micro-RNA designed hairpins," RNA, 2002, 8:842-850.
Schwab et al., "Highly Specific Gene Silencing by Artificial MicroRNAs in Arabidopsis," Plant Cell, 2006, 18:1121-1133.
Zeng et al., "Both Natural and Designed Micro RNAs Can Inhibit the Expression of Cognate mRNAs When Expressed in Human Cells," Mol Cell, 2002, 9:1327-1333.

\* cited by examiner

*Primary Examiner* — Brian Whiteman
(74) *Attorney, Agent, or Firm* — Casimir Jones, S.C.

(57) ABSTRACT

The present invention relates to a method for modulating the expression of epidermal growth factor receptor (EGFR) and its downstream signalling effectors. In particular, the present invention relates to a method for modulating the expression of epidermal growth factor receptor (EGFR) or like molecule in a cell comprising contacting said cell with an agent capable of directly or indirectly interacting with the 3'-untranslated region (UTR) of the mRNA of said EGFR or like molecule, wherein the UTR is encoded by a sequence which comprises a sequence having at least about 70% identity with at least one sequence selected from the group consisting of the sequences set forth in SEQ ID NOs: 1-36.

16 Claims, 13 Drawing Sheets

```
hsa-miR-7    3'       GUUGUUUAGU-GAUC-AGAAGGU
                      | | |  ||| | || |||||||
EGFR A WT    5'...GAUUUUACUUCAAUGGGCUCUUCCA...

EGFR A MT    5'...GAUUUUACUUCAAUGGGCACGUACA...

hsa-miR-7    3'       GUUGUUUU-AGUGAUCAGAAGGU
                      |||| ||  ||| |||||||||
EGFR B WT    5'...AGGAGCACAAGCCACAAGUCUUCCA...

EGFR B MT    5'...AGGAGCACAAGCCACAAGCCCUUCA...

hsa-miR-7    3'       GUUGUUUUAGUGAUCAGAAGGU
                      ||| || |||||  |||||||||
EGFR C WT    5'...UUAGACUGACUUGUUUGUCUUCCA...

EGFR C MT    5'...UUAGACUGACUUGUUUGCCCUUCA...
```

FIGURE 4

| KEGG Pathway | Down | Array | z-score |
|---|---|---|---|
| Glioma | 7 | 64 | 6.40 |
| Endometrial cancer | 6 | 52 | 6.12 |
| Non-small cell lung cancer | 6 | 53 | 6.05 |
| ErbB signaling pathway | 7 | 86 | 5.25 |
| Prostate cancer | 7 | 90 | 5.08 |
| Pancreatic cancer | 6 | 73 | 4.88 |
| Glycerolipid metabolism | 5 | 57 | 4.66 |
| Pyrimidine metabolism | 6 | 84 | 4.41 |
| Renal cell carcinoma | 5 | 68 | 4.11 |
| VEGF signaling pathway | 5 | 68 | 4.11 |
| GnRH signaling pathway | 6 | 95 | 4.01 |
| Melanoma | 5 | 71 | 3.98 |
| Focal adhesion | 9 | 192 | 3.85 |
| Chronic myeloid leukaemia | 5 | 76 | 3.78 |
| Apoptosis | 5 | 84 | 3.49 |
| Colorectal cancer | 5 | 84 | 3.49 |
| Small cell lung cancer | 5 | 86 | 3.42 |
| Epithelial cell signaling in *H. pylori* infection | 4 | 67 | 3.12 |
| Long-term potentiation | 4 | 68 | 3.08 |
| Regulation of actin cytoskeleton | 8 | 202 | 3.06 |
| Melanogenesis | 5 | 99 | 3.03 |
| Fc epsilon RI signaling pathway | 4 | 74 | 2.87 |
| Purine metabolism | 6 | 141 | 2.84 |
| beta-Alanine metabolism | 2 | 24 | 2.83 |
| DNA polymerase | 2 | 25 | 2.75 |
| Dorso-ventral axis formation | 2 | 27 | 2.60 |
| Ether lipid metabolism | 2 | 29 | 2.46 |
| Gap junction | 4 | 90 | 2.40 |
| Urea cycle and metabolism of amino groups | 2 | 30 | 2.40 |
| Olfactory transduction | 2 | 31 | 2.34 |
| Insulin signaling pathway | 5 | 134 | 2.25 |
| Glycerophospholipid metabolism | 3 | 64 | 2.18 |

FIGURE 13

METHOD OF MODULATION OF EXPRESSION OF EPIDERMAL GROWTH FACTOR RECEPTOR(EGFR) INVOLVING MIRNA

RELATED APPLICATIONS

This application is a national stage application, filed under 35 U.S.C. §371, of International Application No. PCT/AU2007/001247, filed on Aug. 28, 2007, which claims the benefit of AU 2006904662 filed Aug. 28, 2006 and AU 2007900558 filed Feb. 6, 2007.

FIELD

The present invention relates to a method for modulating the expression of epidermal growth factor receptor (EGFR) and its downstream signalling effectors. In particular, the present invention relates to a method for modulating the expression of EGFR or like molecule utilizing miRNA or a compound capable of modulating miRNA expression and/or activity.

BACKGROUND

The epidermal growth factor receptor (EGFR), a member of the erbB receptor family, is widely expressed in human tissues and regulates important cellular processes including proliferation, differentiation and development (S. Yano et al., 2003, *Anticancer Res.* 23, 3639). EGFR over-expression occurs in a range of solid tumors and is associated with disease progression, resistance to chemotherapy and radiation therapy, and poor prognosis (Arteaga, 2001, *J. Clin. Oncol.*, 19, 32). Consequently, the EGFR and its downstream signaling effectors are major targets of new therapeutics such as monoclonal antibodies and tyrosine kinase inhibitors (Arteaga, 2003, *Semin. Oncol.*, 30, 3). However, clinical responses to existing anti-EGFR agents in cancer are often limited and thus a major research focus is the development of novel approaches to block EGFR expression and signaling (Bianco et al., 2005, *Cancer*, 12, 159).

MicroRNAs (miRNAs) are short, endogenous, non-coding RNA molecules that bind via imperfect complementarity to 3'-untranslated regions (3'-UTRs) of target mRNAs, causing translational repression of the target gene or degradation of the target mRNA (Bartel, 2004, *Cell.* 116, 281; Mattick & Makunin, 2005, *Hum. Mol. Genet.* 14, 121; Humphreys et al., 2005, *Proc. Natl. Acad. Sci. USA.* 102, 16961). mRNAs are involved in a range of processes that include development and differentiation (Chen et al., 2006, *Nat. Genet.*, 38, 228), proliferation and apoptosis (Cheng et al., 2005, *Nucleic Acids Res.* 33, 1290), and have been implicated in cancer (Zhang et al., 2007, *Dev. Biol.* 302, 1). Interestingly, more than half of miRNA genes are located at sites in the human genome that are frequently amplified, deleted or rearranged in cancer (Calin et al., 2004, *Proc. Natl. Acad. Sci. U.S.A.* 101, 2999), suggesting that some miRNAs may act as oncogenes ('oncomirs', Esquela-Kerscher & Slack, 2006, *Nat. Rev. Cancer* 6, 259) or tumour suppressors (reviewed in Zhang et al., 2007, *Dev. Biol.* 302, 1). For instance, reduced expression of the let-7 family of miRNAs is associated with increased Ras oncogene expression and reduced survival in patients with non-small cell lung cancer (NSCLC) (Johnson et al., 2005, *Cell* 120, 635; Takamizawa et al., 2004, *Cancer Res.*, 64, 3753). In contrast, increased miR-21 expression in gliomas (Chan et al., 2005, Cancer Res. 65, 6029), breast, colon, lung, pancreas, prostate and stomach cancers (Volinia et al., 2006, *Proc. Natl. Acad. Sci. USA.*, 103, 2257) is associated with resistance to apoptosis, reduced chemosensitivity and increased tumor growth (Chan et al., 2005, *Cancer Res.* 65, 6029; Si et al., 2006, Oncogene, 26, 2799).

Computational approaches have been developed to predict miRNA targets. These methods have utilized criteria such as complementarity between target mRNAs and a 'seed' region within the miRNA thought to be critical for binding specificity, and conservation of predicted miRNA-binding sites across 3'-UTRs from multiple species (reviewed in Rajewsky, 2006, *Nat. Genet.*, 38, 8; Maziere & Enright, 2007, *Drug Discov. Today*, 12, 452). It has been suggested that miRNAs may have the capacity to regulate hundreds or even thousands of target mRNAs (Lewis et al., 2005, *Cell*, 120, 15) and that much of this regulation might occur at the level of mRNA decay (Krutzfeldt, et al., 2005, *Nature*, 438, 685). Furthermore, specific miRNAs have the potential to regulate expression of several members of a signaling pathway or cellular process (Stark et al., 2003, *PLoS Biol.*, 1, 60). However, the imperfect complementarity of miRNA:target interactions means that the identification and functional validation of true miRNA targets remains a major challenge.

SUMMARY

Inventors have found that a particular portion of the 3'-untranslated region (3'-UTR) of the epidermal growth factor receptor (EGFR) mRNA controls the expression and/or activity of the EGFR. Moreover, they have identified miRNA species that are capable of modulating the expression and/or activity of the EGFR as well as a number of downstream elements associated with EGFR. These capabilities mean that these miRNA species can play a key regulator role in the EGFR signalling pathway as well as a broad range of functional capacity in multiple cellular synthetic pathways.

Accordingly, in a first aspect the present invention provides a method for modulating the expression of epidermal growth factor receptor (EGFR) or like molecule in a cell comprising contacting said cell with an agent capable of directly or indirectly interacting with the 3'-untranslated region (UTR) of the mRNA of said EGFR or like molecule, wherein the 3'-UTR is encoded by a sequence which comprises a sequence having at least about 70% sequence identity with at least one sequence selected from the group consisting of the sequences set forth in SEQ ID NOs:1-36.

In some embodiments the 3'-UTR comprises a sequence which is encoded by a sequence having at least about 90% identity with at least one sequence selected from the group consisting of the sequences set forth in SEQ ID NOs:1-11. In some embodiments, the 3'-UTR is encoded by a sequence contained within the sequence set forth in SEQ ID NO:1.

In some embodiments the agent is selected from the group consisting of a nucleic acid molecule, an antagomir, an antibody and a compound, wherein said agent specifically binds to mRNA encoded by at least one sequence selected from the group consisting of the sequences set forth in SEQ ID NOs: 1-36. In some embodiments, the agent comprises a first nucleic acid molecule encoding an miRNA precursor, which is processed in a cell to form a second nucleic acid molecule which has a sequence of at least one sequence selected from the group consisting of the sequences set forth in SEQ ID NOs:37 to 54.

In a second aspect, the present invention provides a vector comprising a nucleic acid molecule encoding an miRNA precursor, wherein the miRNA precursor encodes at least one sequence selected from the group consisting of the sequences set forth in SEQ ID NOs:20 to 36.

In some embodiments, the miRNA precursor is processed in a cell after transfection to form a nucleic acid molecule which has a sequence of at least one sequence selected from the group consisting of the sequences set forth in SEQ ID NOs:20 to 36. In further embodiments, the vector comprises a promoter and other regulatory sequences which are operably linked to enable miRNA to be expressed.

In a third aspect, the present invention provides a method for modulating the expression of epidermal growth factor receptor (EGFR) or like molecule in a cell comprising contacting said cell with an agent capable of directly or indirectly altering the endogenous expression of at least one nucleic acid molecule encoded by a sequence having a sequence selected from the group consisting of the sequences set forth in SEQ ID NOs:20 to 36.

In some embodiments, the agent increases the endogenous expression of at least one nucleic acid molecule encoding an miRNA species, wherein the expression of EGFR or like molecule is reduced compared to the level of expression before the agent is contacted with the cell.

In some embodiments the agent comprises a nucleic acid molecule, an antagomir, an antibody and a compound which specifically binds to an mRNA encoded by at least one sequence selected from the group consisting of the sequences set forth in SEQ ID NOs:1-36. In some embodiments, the agent comprises a nucleic acid molecule having a sequence selected from the group consisting of the sequences set forth in SEQ ID NOs:37 to 54, wherein the nucleic acid molecule decreases the level of expression of EGFR or like molecule. The agent may further comprise a pharmaceutically acceptable carrier. The agent may be suitable for use in the treatment or prevention of cancer, such as a brain cancer, lung cancer, breast cancer, prostate cancer, or colon cancer. In some embodiments the brain cancer is glioma.

In a fourth aspect the invention provides the use of an agent comprising either a nucleic acid molecule which comprises a sequence having at least about 90% identity with at least one sequence selected from the group consisting of the sequences set forth in SEQ ID NOs:37 to 54 or a compound capable of directly or indirectly modulating the endogenous expression of at least one nucleic acid molecule having a sequence selected from the group consisting of the sequences set forth in SEQ ID NOs: 37 to 54, to modulate the expression of EGFR or like molecule by a cell. In some embodiments the expression of EGFR is decreased.

In a fifth aspect the invention provides a method of modulating growth of a cell expressing EGFR or like molecule, comprising the step of contacting said cell with an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences set forth in SEQ ID NOs:37 to 54, thereby modulating growth of the cell.

In a sixth aspect the invention provides a method of modulating differentiation of a cell expressing EGFR or like molecule, comprising the step of contacting said cell with an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences set forth in SEQ ID NOs:37 to 54, thereby modulating differentiation of the cell.

In a seventh aspect the invention provides the use of an agent comprising either a nucleic acid molecule which comprises a sequence having at least about 90% identity with at least one sequence selected from the group consisting of the sequences set forth in SEQ ID NOs:37 to or a compound capable of directly or indirectly altering the endogenous expression of at least one nucleic acid molecule having a sequence selected from the group consisting of the sequences set forth in SEQ ID NOs:37 to 54 for modulating growth of a cell expressing EGFR or like molecule.

In an eighth aspect the invention provides the use of an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences set forth in SEQ ID NOs:37 to 54, for modulating differentiation of a cell expressing EGFR or like molecule.

In a ninth aspect the invention provides a method of diagnosis of a disease or a disorder associated with an abnormal level of expression of EGFR in a subject, comprising the step of determining the level of expression of at least one sequence selected from the group consisting of the sequences set forth in SEQ ID NOs:37-54 in the subject and comparing said expression level to a reference expression level.

In a tenth aspect the invention provides a method of prognosis of a disease or a disorder associated with an abnormal level of expression of EGFR in a subject, comprising the step of determining the level of expression of at least one sequence selected from the group consisting of the sequences set forth in SEQ ID NOs:37-54 in the subject and comparing said expression level to a reference expression level.

In an eleventh aspect the invention provides the use of an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences forth SEQ ID NOs:37 to 54, for the preparation of a medicament for the treatment or prevention of a disease or disorder associated with an abnormal level of expression of EGFR.

In a twelfth aspect the invention provides the use of an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences set forth in SEQ ID NOs:37 to 54, for the diagnosis of a disease or disorder associated with an abnormal level of expression of EGFR or like molecule.

In a thirteenth aspect the invention provides the use of an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences set forth in SEQ ID NOs:37 to 54, for the prognosis of a disease or disorder associated with an abnormal level of expression of EGFR or like molecule.

In a fourteenth aspect the invention provides a method of treating or preventing a disease or disorder associated with an abnormal level of expression of EGFR or like molecule in a mammalian subject, comprising the step of administering to the subject an agent comprising either a nucleic acid molecule which comprises a sequence having at least about 90% identity with at least one sequence selected from the group consisting of the sequences set forth in SEQ ID NOs:37 to 54 or a compound capable of directly or indirectly altering the endogenous expression of at least one nucleic acid molecule having a sequence selected from the group consisting of the sequences set forth in SEQ ID NOs:37 to 54.

The disease of the fourth to fourteenth aspects may be cancer, such as a brain cancer, lung cancer, breast cancer, prostate cancer, or colon cancer. In some embodiments the cancer is glioma.

The fourteenth aspect may further comprise the administration of a second agent, such as an anti-EGFR monoclonal antibody or an EGFR tyrosine kinase inhibitor. In some embodiments the EGFR tyrosine kinase inhibitor is erlotinib or gefitinib.

In a fifteenth aspect the invention provides a method of screening for an agent or compound capable of modulating the endogenous expression of miRNA, comprising the step of:
  (i) providing a construct comprising at least one nucleic acid molecule having a sequence selected from the group consisting of the sequences set forth in SEQ ID NOs:1 to 36 operably linked to a reporter molecule, wherein said reporter produces a detectable signal; and
  (ii) contacting said construct with a test compound or agent under conditions suitable for binding between the at least one nucleic acid molecule and the compound and/or agent, wherein binding between the molecule and the test compound or agent reduces the detectable signal.

BRIEF DESCRIPTION OF THE FIGURES

FIG. 4 shows the sequence of wild type (WT) and mutant (MT) EGFR mRNA 3'-UTR miR-7 target sites. The hsa-miR-7 sequence used in the alignment corresponds to SEQ ID NO: 80. The figure shows gaps (dashed line) in the has-miR-7 sequence introduced by its alignment with the EGFR-A WT sequence. EGFR A WT, EGFR B WT and EGFR C WT sequences used in the alignment correspond to SEQ ID NO's: 81, 83 and 85 respectively. The EGFR A MT, EGFR B MT and EGFR C MT sequences used in the alignment correspond to SEQ ID NO's: 82, 84 and 86 respectively.

FIG. 13 shows the identification of functional pathways enriched for miR-7 target genes. KEGG pathways significantly enriched for genes down regulated in A549 cells by miR-7 transfection compared to miR-NC transfection include: "Glioma", "ErbB signalling pathway", GnRH signalling pathway", "Long-term potentiation", and "Gap junction". $Z > 1.96$ for $p < 0.05$.

DETAILED DESCRIPTION OF PREFERRED EMBODIMENTS

Figure 1:
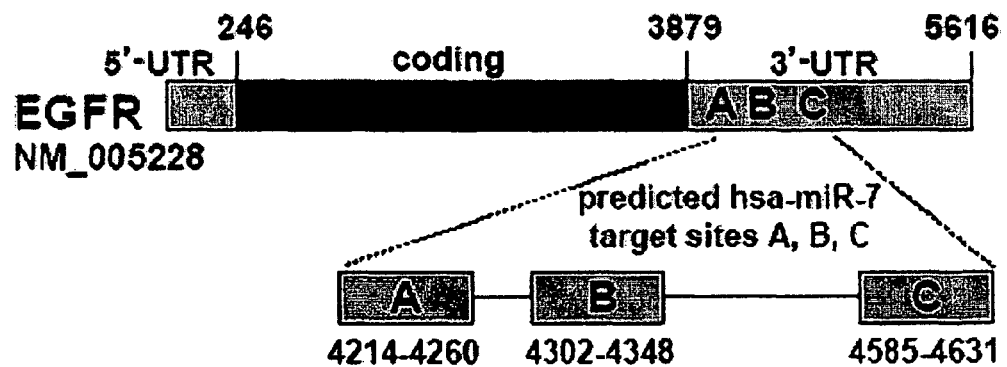
FIG. 1 show the non-conserved EGFR 3'-UTR mRNA contains target sites for specific binding of miR-7. By using TargetScan™ software three miR-7 binding sites (A, B, C) in human EGFR mRNA 3'-UTR were predicted.

Before describing the invention in detail, it is to be understood that it is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional molecular biology and pharmacology within the skill of the art. Such techniques are well known to the skilled worker, and are explained fully in the literature. See, eg., "Molecular Cloning: A Laboratory Manual", $2^{nd}$ Ed., (ed. by Sambrook, Fritsch and Maniatis) (Cold Spring Harbor Laboratory Press: 1989); "Nucleic Acid Hybridization", (Hames & Higgins eds. 1984); "Oligonucleotide Synthesis" (Gait ed., 1984); Remington's Pharmaceutical Sciences, $17^{th}$ Edition, Mack Publishing Company, Easton, Pa., USA.; "The Merck Index", $12^{th}$ Edition (1996), Therapeutic Category and Biological Activity Index; and "Transcription & Translation", (Hames & Higgins eds. 1984).

Throughout the specification, the word "comprise" and variations of the word, such as "comprising" and "comprises", means "including but not limited to" and is not intended to exclude other additives, components, integers or steps. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

It must be noted that as used herein and in the appended claims, the singular forms "a," "an," and "the" include plural reference unless the context clearly dictates otherwise. Thus, for example, a reference to "a nucleic acid molecule" includes a plurality of nucleic acid molecules, and a reference to "a cell" is a reference to one or more cells, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In one of its broadest aspects, the present invention relates to the epidermal growth factor receptor (EGFR) and like molecules. The EGFR is a member of the erbB receptor family and is widely expressed in mammalian tissues and regulates important cellular processes including proliferation, differentiation and development (Yano et al., 2003, Anticancer Res. 23, 3639). The gene encoding EGFR herein after referred to as "EGFR gene" is well-known in the art. Non-limiting examples of EGFR genes include the sequences disclosed in GenBank Accession numbers, XM_001156439.1 (Pan troglodytes), XM_001156495.1 (Pan troglodytes), XM_001156546.1 (Pan troglodytes), XM_519102.2 (Pan troglodytes), NM-005228.3 (*Homo sapiens*), AY588246.1 (*Homo sapiens*), AC073324.6 (*Homo sapiens*), AC146013.2 (Pan troglodytes), AF288738.1 (*Homo sapiens*), X00588.1 (*Homo sapiens*) and NM_214007.1 (*Sus scrofa*), herein incorporated by reference. As such, the term "EGFR or like molecule," as used herein, refers to a gene capable of transcribing an mRNA transcript having substantial homology with an mRNA transcribed from any one of the genes for EGFR as set forth in any one of the above sequences shown in Genbank.

In some embodiments of the present invention the term "EGFR or like molecule" refers to the 3'-untranslated region (UTR) of the mRNA encoding EGFR or like molecule. In these embodiments, the 3'-UTR of EGFR mRNA or like molecule is encoded by at least one of the sequences selected from the group consisting of SEQ ID NO:1 to 36 or a sequence with a high degree of sequence identity thereto. As can be seen from Table 1, the cDNA encoding the 3'-UTR's of EGFR mRNA from a number of mammalian

TABLE 1

| SEQ ID NO: 1 | 1 | TTTCATTGTCGCTATTGATTTTTACTTCAATGGGCTCTTCCAACAAGGAAGAAGCTTGCT | 60 |
| --- | --- | --- | --- |
| SEQ ID NO: 2 | 4044 | TTTCATTGTCGCTATTGATTTTTACTTCAATGGGCTCTTCCAACAAGGAAGAAGCTTGCT | 4103 |
| SEQ ID NO: 3 | 4278 | TTTCATTGTCGCTATTGATTTTTACTTCAATGGGCTCTTCCAACAAGGAAGAAGCTTGCT | 4337 |
| SEQ ID NO: 4 | 4233 | TTTCATTGTCGCTATTGATTTTTACTTCAATGGGCTCTTCCAACAAGGAAGAAGCTTGCT | 4292 |
| SEQ ID NO: 5 | 4227 | TTTCATTGTCGCTATTGATTTTTACTTCAATGGGCTCTTCCAACAAGGAAGAAGCTTGCT | 4286 |
| SEQ ID NO: 6 | 4214 | TTTCATTGTCGCTATTGATTTTTACTTCAATGGGCTCTTCCAACAAGGAAGAAGCTTGCT | 4273 |
| SEQ ID NO: 7 | 188790 | TTTCATTGTCGCTATTGATTTTTACTTCAATGGGCTCTTCCAACAAGGAAGAAGCTTGCT | 188849 |
| SEQ ID NO: 8 | 18261 | TTTCATTGTCGCTATTGATTTTTACTTCAATGGGCTCTTCCAACAAGGAAGAAGCTTGCT | 18320 |
| SEQ ID NO: 9 | 476 | TTTCATTGTCGCTATTGATTTTTACTTCAATGGGCTCTTCCAACAAGGAAGAAGCTTGCT | 535 |
| SEQ ID NO: 10 | 196065 | TTTCATTGTCGCTATTGATTTTTACTTCAATGGGCTCTTCCAACAAGGAAGAAGCTTGCT | 196124 |
| SEQ ID NO: 11 | 4156 | TTTCATTGTCGCTATTGATTTTTACTTCAATGGGCTCTTCCAACAAGGAAGAAGCTTGCT | 4215 |

TABLE 1-continued

| SEQ ID NO: 1 | 61 | GGTAGCACTTGCTACCCTGAGTTCATCCAGGCCCAACTGTGAGCAAGGAGCACAAGCCAC | 120 |
|---|---|---|---|
| SEQ ID NO: 2 | 4104 | GGTAGCACTTGCTACCCTGAGTTCATCCAGGCCCAACTGTGAGCAAGGAGCACAAGCCAC | 4163 |
| SEQ ID NO: 3 | 4338 | GGTAGCACTTGCTACCCTGAGTTCATCCAGGCCCAACTGTGAGCAAGGAGCACAAGCCAC | 4397 |
| SEQ ID NO: 4 | 4293 | GGTAGCACTTGCTACCCTGAGTTCATCCAGGCCCAACTGTGAGCAAGGAGCACAAGCCAC | 4352 |
| SEQ ID NO: 5 | 4287 | GGTAGCACTTGCTACCCTGAGTTCATCCAGGCCCAACTGTGAGCAAGGAGCACAAGCCAC | 4346 |
| SEQ ID NO: 6 | 4274 | GGTAGCACTTGCTACCCTGAGTTCATCCAGGCCCAACTGTGAGCAAGGAGCACAAGCCAC | 4333 |
| SEQ ID NO: 7 | 188850 | GGTAGCACTTGCTACCCTGAGTTCATCCAGGCCCAACTGTGAGCAAGGAGCACAAGCCAC | 188909 |
| SEQ ID NO: 8 | 18321 | GGTAGCACTTGCTACCCTGAGTTCATCCAGGCCCAACTGTGAGCAAGGAGCACAAGCCAC | 18380 |
| SEQ ID NO: 9 | 536 | GGTAGCACTTGCTACCCTGAGTTCATCCAGGCCCAACTGTGAGCAAGGAGCACAAGCCAC | 595 |
| SEQ ID NO: 10 | 196125 | GGTAGCACTTGCTACCCTGAGTTCATCCAGGCCCAACTGTGAGCAAGGAGCACAAGCCAC | 196184 |
| SEQ ID NO: 11 | 4216 | GGTAGCACTTGCTACCCTGAGTTCATCCAGGCCCAACTGTGAGCAAGGAGCACAAGCCAC | 4275 |
| SEQ ID NO: 1 | 121 | AAGTCTTCCAGAGGATGCTTGATTCCAGTGGTTCTGCTTCAAGGCTTCCACTGCAAAACA | 180 |
| SEQ ID NO: 2 | 4164 | AAGTCTTCCAGAGGATGCTTGATTCCAGTGGTTCTGCTTCAAGGCTTCCACTGCAAAACA | 4223 |
| SEQ ID NO: 3 | 4398 | AAGTCTTCCAGAGGATGCTTGATTCCAGTGGTTCTGCTTCAAGGCTTCCACTGCAAAACA | 4457 |
| SEQ ID NO: 4 | 4353 | AAGTCTTCCAGAGGATGCTTGATTCCAGTGGTTCTGCTTCAAGGCTTCCACTGCAAAACA | 4412 |
| SEQ ID NO: 5 | 4347 | AAGTCTTCCAGAGGATGCTTGATTCCAGTGGTTCTGCTTCAAGGCTTCCACTGCAAAACA | 4406 |
| SEQ ID NO: 6 | 4334 | AAGTCTTCCAGAGGATGCTTGATTCCAGTGGTTCTGCTTCAAGGCTTCCACTGCAAAACA | 4393 |
| SEQ ID NO: 7 | 188910 | AAGTCTTCCAGAGGATGCTTGATTCCAGTGGTTCTGCTTCAAGGCTTCCACTGCAAAACA | 188969 |
| SEQ ID NO: 8 | 18381 | AAGTCTTCCAGAGGATGCTTGATTCCAGTGGTTCTGCTTCAAGGCTTCCACTGCAAAACA | 18440 |
| SEQ ID NO: 9 | 596 | AAGTCTTCCAGAGGATGCTTGATTCCAGTGGTTCTGCTTCAAGGCTTCCACTGCAAAACA | 655 |
| SEQ ID NO: 10 | 196185 | AAGTCTTCCAGAGGATGCTTGATTCCAGTGGTTCTGCTTCAAGGCTTCCACTGCAAAACA | 196244 |
| SEQ ID NO: 11 | 4276 | AAGTCTTCCAGAGGATGCTTGATTCCAGTGGTTCTGCTTCAAGGCTTCCACTGCAAAACA | 4335 |
| SEQ ID NO: 1 | 181 | CTAAAGATCCAAGAAGGCCTTCATGGCCCCAGCAGGCCGGATCGGTACTGTATCAAGTCA | 240 |
| SEQ ID NO: 2 | 4224 | CTAAAGATCCAAGAAGGCCTTCATGGCCCCAGCAGGCCGGATCGGTACTGTATCAAGTCA | 4283 |
| SEQ ID NO: 3 | 4458 | CTAAAGATCCAAGAAGGCCTTCATGGCCCCAGCAGGCCGGATCGGTACTGTATCAAGTCA | 4517 |
| SEQ ID NO: 4 | 4413 | CTAAAGATCCAAGAAGGCCTTCATGGCCCCAGCAGGCCGGATCGGTACTGTATCAAGTCA | 4472 |
| SEQ ID NO: 5 | 4407 | CTAAAGATCCAAGAAGGCCTTCATGGCCCCAGCAGGCCGGATCGGTACTGTATCAAGTCA | 4466 |
| SEQ ID NO: 6 | 4394 | CTAAAGATCCAAGAAGGCCTTCATGGCCCCAGCAGGCCGGATCGGTACTGTATCAAGTCA | 4453 |
| SEQ ID NO: 7 | 188970 | CTAAAGATCCAAGAAGGCCTTCATGGCCCCAGCAGGCCGGATCGGTACTGTATCAAGTCA | 189029 |
| SEQ ID NO: 8 | 18441 | CTAAAGATCCAAGAAGGCCTTCATGGCCCCAGCAGGCCGGATCGGTACTGTATCAAGTCA | 18500 |
| SEQ ID NO: 9 | 656 | CTAAAGATCCAAGAAGGCCTTCATGGCCCCAGCAGGCCGGATCGGTACTGTATCAAGTCA | 715 |
| SEQ ID NO: 10 | 196245 | CTAAAGATCCAAGAAGGCCTTCATGGCCCCAGCAGGCCGGATCGGTACTGTATCAAGTCA | 196304 |
| SEQ ID NO: 11 | 4336 | CTAAAGATCCAAGAAGGCCTTCATGGCCCCAGCAGGCCGGATCGGTACTGTATCAAGTCA | 4395 |
| SEQ ID NO: 1 | 241 | TGGCAGGTACAGTAGGATAAGCCACTCTGTCCCTTCCTGGGCAAAGAAGAAACGGAGGGG | 300 |
| SEQ ID NO: 2 | 4284 | TGGCAGGTACAGTAGGATAAGCCACTCTGTCCCTTCCTGGGCAAAGAAGAAACGGAGGGG | 4343 |
| SEQ ID NO: 3 | 4518 | TGGCAGGTACAGTAGGATAAGCCACTCTGTCCCTTCCTGGGCAAAGAAGAAACGGAGGGG | 4577 |
| SEQ ID NO: 4 | 4473 | TGGCAGGTACAGTAGGATAAGCCACTCTGTCCCTTCCTGGGCAAAGAAGAAACGGAGGGG | 4532 |
| SEQ ID NO: 5 | 4467 | TGGCAGGTACAGTAGGATAAGCCACTCTGTCCCTTCCTGGGCAAAGAAGAAACGGAGGGG | 4526 |
| SEQ ID NO: 6 | 4454 | TGGCAGGTACAGTAGGATAAGCCACTCTGTCCCTTCCTGGGCAAAGAAGAAACGGAGGGG | 4513 |
| SEQ ID NO: 7 | 189030 | TGGCAGGTACAGTAGGATAAGCCACTCTGTCCCTTCCTGGGCAAAGAAGAAACGGAGGGG | 189089 |
| SEQ ID NO: 8 | 18501 | TGGCAGGTACAGTAGGATAAGCCACTCTGTCCCTTCCTGGGCAAAGAAGAAACGGAGGGG | 18560 |
| SEQ ID NO: 9 | 716 | TGGCAGGTACAGTAGGATAAGCCACTCTGTCCCTTCCTGGGCAAAGAAGAAACGGAGGGG | 775 |
| SEQ ID NO: 10 | 196305 | TGGCAGGTACAGTAGGATAAGCCACTCTGTCCCTTCCTGGGCAAAGAAGAAACGGAGGGG | 196364 |
| SEQ ID NO: 11 | 4396 | TGGCAGGTACAGTAGGATAAGCCACTCTGTCCCTTCCTGGGCAAAGAAGAAACGGAGGGG | 4455 |

TABLE 1-continued

| | | | |
|---|---|---|---|
| SEQ ID NO: 1 | 301 | ATGGAATTCTTCCTTAGACTTACTTTTGTAAAAATGTCCCCACGGTACTTACTCCCCACT | 360 |
| SEQ ID NO: 2 | 4344 | ATGGAATTCTTCCTTAGACTTACTTTTGTAAAAATGTCCCCACGGTACTTACTCCCCACT | 4403 |
| SEQ ID NO: 3 | 4578 | ATGGAATTCTTCCTTAGACTTACTTTTGTAAAAATGTCCCCACGGTACTTACTCCCCACT | 4637 |
| SEQ ID NO: 4 | 4533 | ATGGAATTCTTCCTTAGACTTACTTTTGTAAAAATGTCCCCACGGTACTTACTCCCCACT | 4592 |
| SEQ ID NO: 5 | 4527 | ATGGAATTCTTCCTTAGACTTACTTTTGTAAAAATGTCCCCACGGTACTTACTCCCCACT | 4586 |
| SEQ ID NO: 6 | 4514 | ATGGAATTCTTCCTTAGACTTACTTTTGTAAAAATGTCCCCACGGTACTTACTCCCCACT | 4573 |
| SEQ ID NO: 7 | 189090 | ATGGAATTCTTCCTTAGACTTACTTTTGTAAAAATGTCCCCACGGTACTTACTCCCCACT | 189149 |
| SEQ ID NO: 8 | 18561 | ATGGAATTCTTCCTTAGACTTACTTTTGTAAAAATGTCCCCACGGTACTTACTCCCCACT | 18620 |
| SEQ ID NO: 9 | 776 | ATGGAATTCTTCCTTAGACTTACTTTTGTAAAAATGTCCCCACGGTACTTACTCCCCACT | 835 |
| SEQ ID NO: 10 | 196365 | AT-GAATTCTTCCTTAGACTTACTTTTGTAAAAATGTCCCCACGGTACTTACTCCCCACT | 196423 |
| SEQ ID NO: 11 | 4456 | AT-GAATTCTTCCTTAGACTTACTTTTGTAAAAATGTCCCCACGGTACTTACTCCCCACT | 4514 |
| | | | |
| SEQ ID NO: 1 | 361 | GATGGACCAGTGGTTTCCAGTCATGAGCGTTAGACTGACTTGTTTGTCTTCCATTCCA | 418 |
| SEQ ID NO: 2 | 4404 | GATGGACCAGTGGTTTCCAGTCATGAGCGTTAGACTGACTTGTTTGTCTTCCATTCCA | 4461 |
| SEQ ID NO: 3 | 4636 | GATGGACCAGTGGTTTCCAGTCATGAGCGTTAGACTGACTTGTTTGTCTTCCATTCCA | 4695 |
| SEQ ID NO: 4 | 4593 | GATGGACCAGTGGTTTCCAGTCATGAGCGTTAGACTGACTTGTTTGTCTTCCATTCCA | 4650 |
| SEQ ID NO: 5 | 4587 | GATGGACCAGTGGTTTCCAGTCATGAGCGTTAGACTGACTTGTTTGTCTTCCATTCCA | 4644 |
| SEQ ID NO: 6 | 4574 | GATGGACCAGTGGTTTCCAGTCATGAGCGTTAGACTGACTTGTTTGTCTTCCATTCCA | 4631 |
| SEQ ID NO: 7 | 189150 | GATGGACCAGTGGTTTCCAGTCATGAGCGTTAGACTGACTTGTTTGTCTTCCATTCCA | 189207 |
| SEQ ID NO: 8 | 18621 | GATGGACCAGTGGTTTCCAGTCATGAGCGTTAGACTGACTTGTTTGTCTTCCATTCCA | 18678 |
| SEQ ID NO: 9 | 836 | GATGGACCAGTGGTTTCCAGTCATGAGCGTTAGACTGACTTGTTTGTCTTCCATTCCA | 894 |
| SEQ ID NO: 10 | 196424 | GATGGACCAGTGGTTTCCAGTCATGAGCGTTAGACTGACTTGTTTGTCTTCCATTCCA | 196481 |
| SEQ ID NO: 11 | 4515 | GATGGACCAGTGGTTTCCAGTCATGAGCGTTAGACTGACTTGTTTGTCTTCCATTCCA | 4572 | species have a high degree of sequence identity. The term "sequence identity" or "percentage of sequence identity" may be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences.

Identity and similarity of related nucleic acid molecules can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biolog, von Heinje, G., Academic Press, 1987; Sequence Analysis Primer, Gribskov, M. and Devereux, J., eds., M. Stockton Press, New York, 1991; and Carillo et al., SIAM J. Applied Math. 48:1073, 1988.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387, 1984; Genetics Computer Group, University of Wisconsin, Madison, Wis.), BLASTP, BLASTN, and FASTA (Altschul et al., J. Mol. Biol., 215:403-410, 1990). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Preferred parameters for nucleic acid molecule sequence comparison include the following:
Algorithm: Needleman and Wunsch, J. Mol. Biol. 48:443-4, 1970
Comparison matrix: matches=+10, mismatch=0
Gap Penalty: 50
Gap Length Penalty: 3

The GAP program is also useful with the above parameters.

The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will be apparent to those of-skill in the art and will depend on the specific comparison to be made.

Typically, the sequence encoding the 3'-UTR of EGFR mRNA or like molecule in accordance with the present invention will show at least 70%, preferably 80%, 85%, 90%, 91%, 92%, 93%, 94%, 95%, 96%, 97%, 98%, or 99% sequence identity with one or more of the sequences shown in SEQ ID NO:1 to 36. More particularly, the sequence encoding the 3'-UTR of EGFR mRNA or like molecule will show 100% sequence identity with one or more of the sequences shown in SEQ ID NO:20-36. As such, the term "3'-UTR," as used herein, refers to the sequence encoding any of the 3'-UTRs of EGFR mRNA such as those shown in SEQ ID NO: 1 to 36 or like molecule ie a molecule which comprises a sequence with a high sequence identity to one or more of the sequences shown in SEQ ID NO: 1 to 36 or any molecule with a high degree of sequence identity to these sequences.

In some embodiments, the 3'-UTR of the EGFR or like molecule comprises a "3'-UTR motif" which is a specific sequence contained within the sequences shown in SEQ ID NO:1 to 19. For example, as shown in the Examples supra, the inventors have identified that particular portions or regions of the 3'-UTR of EGFR mRNA or like molecule comprise motifs that have high degrees of sequence identity. Non-limiting examples of these motifs include the sequences shown in SEQ ID NO:31-36. These motifs encode binding sites for specific miRNA species.

As used herein, an "miRNA molecule" or "miRNA species" is a small RNA molecule, typically about 20 to 25 nucleotides, encoded by the genome of an animal or produced synthetically with a sequence which corresponds to one encoded by the genome of the animal. As used herein, miRNA molecules may be single-stranded or double-stranded (also known as siRNA but included within the scope of this invention). In some embodiments of the invention the miRNA is a single-stranded miRNA molecule.

Micro RNA molecules regulate the expression of their target(s) by one of two mechanisms: either by perfect or near perfect binding to the mRNA target and induction of miRNA-associated, multiprotein RNA-induced-silencing complex (miRISC), which results in accelerated mRNA decay, or by less perfect binding to the target mRNA and inhibition of translation through a RISC complex similar to, or identical with, the complex recruited in RNA interference (RNAi).

In some embodiments, the miRNA molecules of the present invention have the sequences shown in shown in SEQ ID Nos:37-53. In some embodiments of the present invention, these miRNA species are termed "miR-7". Without wishing to be bound by any theory or hypothesis, the invention is based on the discovery that the particular species of miRNA, for example, miR-7, specifically binds the 3'-UTR of mRNA encoding the EGFR or like molecule. Moreover, the inventors have surprisingly discovered that over-expression of these miRNA's like miR-7 in cancer cells with elevated EGFR expression results in a reduced level of EGFR mRNA and protein expression, G1 phase cell cycle arrest and cell death.

In some embodiments, the miRNA species has the sequence 5' UGGAAGACUAGUGAUUUUGUUG 3' (SEQ ID NO:48) and includes molecules with at least 80% sequence identity to SEQ ID NO:48. In some embodiments, the miRNA species has at least 90% sequence identity to SEQ ID NO:48. In other embodiments, the miRNA species has at least 95% sequence identity to SEQ ID NO:48. In other embodiments, the miRNA species has at least 98% sequence identity to SEQ ID NO:48. In still other embodiments, the miRNA species has at least 99% sequence identity to SEQ ID NO:48.

In addition to binding the 3'-UTR of EGFR mRNA, the inventors have shown that any mRNA molecule comprising the 3'-UTR motif CTCTTCCA (SEQ ID NO:31), CTTTTCCA (SEQ ID NO:32), CTCTTGTA (SEQ ID NO:33), GTCTTCCA (SEQ ID NO:34), GTCTTCCA (SEQ ID NO:35) or GTTTTCTG (SEQ ID NO:36) are capable of binding the miRNA species of the present invention. Indeed, the Raf-1 serine/threonine kinase (murine leukemia viral oncogene homolog 1), a key regulator in many growth and developmental pathways, is capable of binding miR-7. The regulation of Raf-1 is an intricate multistep process involving changes in Raf-1 subcellular localization and changes in protein-protein interactions in response to phosphorylation events.

In addition to the full-length miR-7 molecule, such as that shown in SEQ ID NO:48, the term "miR-7" also includes fragments of a miR-7 molecule provided the fragments are functional fragments. The term "fragment" of an miRNA molecule means a portion of the full-length molecule. The size of the fragment is limited only in that it must be a functional fragment, that is, able to modulate the expression of EGFR, modulate cell growth, and/or modulate cell differentiation. Typically, it will comprise at least the sequence shown in SEQ ID NO:52.

As mentioned above, the inventors have surprisingly found that expression of EGFR can be modulated by using an agent to directly or indirectly interact with the 3'-UTR of the mRNA of EGFR or like molecule. The term "agent" comprises any nucleic acid molecule, antagomir, antibody or compound that is capable of interacting e.g. binding, to the 3'-UTR of the mRNA of EGFR or like molecule.

The term "modulator," "modulation," "modulating" and grammatical equivalents as used herein refers to the agent as described herein which is capable of affecting directly or indirectly the activity or expression level of EGFR or like molecule such that the activity or expression is altered when compared to "wild-type" activity or expression i.e. activity or expression before contacting with an agent of the present invention. The term "indirectly" refers to the mode of action of an agent, wherein the effect is mediated via an intermediary molecule rather than through direct contact with the 3'-UTR. In contrast, the term "directly" refers to an agent that interacts with the 3'-UTR of the EGFR mRNA or like molecule by, for example, binding to the 3'-UTR.

In some embodiments the present invention provides a method of modulating the expression of EGFR in a cell by contacting the cell with an agent eg miRNA species as defined herein. The term "cell" refers to any type of cell which expresses EGFR or like molecule. Examples of cells which express EGFR include cancer cells, lung cells, bone cells, blood cells, and skin cells. The cell may be isolated or purified from a mammalian subject, may be located in a sample from a subject, or may be located in or on a subject.

The term "sample" as used herein includes any biological material of a subject which contains a cell comprising nucleic acid molecules encoding EGFR. In some embodiments the sample is a tissue, or fluid such as bone marrow, plasma, serum, spinal fluid, lymph fluid, the sections of the respiratory, intestinal, or genitourinary tracts, tears, saliva, milk, whole blood, tumours, organs. In some embodiments the sample is blood.

Contacting the cell and the agents eg miRNA species or a functional fragment thereof, or a nucleic acid molecule antisense thereto, or an antagomir or antibody which specifically binds the miRNA species, or a compound which modulates transcription of DNA encoding the miRNA species may be achieved by any method known in the art. In some embodiments the cell has been isolated from the subject and combining the cell and the miRNA species or a functional fragment thereof, or a nucleic acid molecule antisense thereto, or an antagomir or antibody which specifically binds miRNA, or compound which modulates transcription of DNA encoding miRNA species occurs in vitro. In other embodiments the cell has not been isolated from the subject and contacting the cell and the miRNA species et cetera occurs in vivo. The agent may be contacted with the cell directly, ie applied directly to a cell requiring modulation of EGFR. Alternatively the agent may be combined with the cell indirectly, eg by injecting the miRNA species into the bloodstream of a subject, which then carries the miRNA species to the cell requiring modulation of EGFR.

In some embodiments, the agent of the present invention is contacted with a cell, wherein the endogenous levels of one or more miRNA species of the present invention are expressed differently as compared to the cell before contacting with the agent. The term "endogenous" as used herein refers to the "naturally-occurring" levels of expression and/or activity of, for example, one or more of the miRNA species of the present invention (eg SEQ ID NO:37-54). In these embodiments, compounds or compositions can be contacted with cells such that the expression and/or activity of the miRNA species of the present invention are increased or decreased as compared to the "naturally-occurring" levels of one or more miRNA species of the present invention (e.g., SEQ ID NO:37-54) and/or miRNA activity as compared to the wild-type and/or normal levels.

When the miRNA species are administered to a subject, in some embodiments this is via a vector (eg viral)-based approach, or by administration of the miRNA in the form of a fusion protein where the miRNA is bound to a protamine-Fab antibody fragment which targets the miRNA to cells of interest, ie cells expressing miRNA species of the present invention.

Alternatively, a sample may be removed from a subject and combined with the miRNA in vitro prior to returning at least a portion of the sample back to the subject. For example, the sample may be a blood sample which is removed from a subject and combined with the miRNA prior to injecting at least a portion of the blood back into the subject.

Alternatively the sample may be combined in vivo or in vitro with a nucleic acid molecule which is antisense to the miRNA species, an antagomir which specifically binds the miRNA, an antibody which specifically binds the miRNA, and/or a compound which modulates transcription of DNA encoding one or more of the miRNA species.

An antisense nucleic acid molecule has a sequence complementary to the sequence of another nucleic acid molecule. Thus, an antisense molecule of some embodiments of the invention has the complementary sequence to an miRNA species. The antisense molecule may be 100% complementary to, for example, miR-7, or may be less than 100% complementary to the miR-7 provided that the antisense molecule is able to inhibit the function of the miR-7 molecule, for example, inhibit binding of the miR-7 molecule to EGFR mRNA.

An "antagomir" is a short RNA molecule which has been designed to have a sequence complementary to a specific miRNA, such as, for example, any one of sequences SEQ ID NO:37-54, and which is conjugated with cholesterol. An antagomir binds to its specific target miRNA and this interaction inhibits the miRNA's activity. As mentioned above, the nucleic acid molecule may be 100% complementary to, for example, miR-7 molecule or may be less than 100% complementary provided that the antisense molecule is able to inhibit the function of miR-7.

The term "antibody" is used in the broadest sense and specifically covers anti-miR-7 polyclonal and monoclonal antibodies (including agonist, antagonist, and neutralizing antibodies), anti-miR-7 antibody compositions with polyepitopic specificity, single chain anti-miRNA antibodies, and functional fragments of anti-miRNA antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies; single-chain antibody molecules; and multispecific antibodies formed from antibody fragments.

In some embodiments of the invention combining the miRNA species or a nucleic acid molecule antisense thereto, or an antagomir or antibody which specifically binds to the miRNA and/or a compound which modulates transcription of DNA encoding one or more of the miRNA species, modulates the level of expression of EGFR or like molecule. The term "expression level" refers to the level of translation of an mRNA molecule and also encompasses the absence of expression.

The EGFR expression level may be increased compared to the level in a sample which has not been combined with an miRNA species of the present invention. Alternatively, the expression level of a nucleic acid molecule may be decreased compared to the level in a sample of a subject which has not been combined with an miRNA species of the present invention.

EGFR binds to EGF, TGF-α, and other related proteins, leading to the generation of proliferative and survival signals within the cell. It is found on the surface of some cells and, when bound by EGF, causes the cells to grow and differentiate. Thus in some embodiments the invention provides a method of modulating cell growth. As used herein the term "cell growth" means growth of a cell in number, such as by reproduction of a parent cell to produce daughter cells, and/or growth in size.

In some embodiments the invention provides a method of modulating cell differentiation. As used herein the term "cell differentiation" refers to a process whereby a relatively young, immature, cell type reaches a specialised form and/or function.

EGFR is found at abnormal levels on the surface of many types of cells, including cancer cells. Thus in some embodiments the invention provides the administration of miRNA species of the present invention or a functional fragment thereof, or a nucleic acid molecule antisense thereto, or an antagomir or antibody which specifically binds one or more of the miRNA species, or a compound which modulates transcription of DNA encoding miRNA species of the present invention, to treat or prevent a disease or disorder associated with an abnormal level of expression of EGFR by a subject.

The miRNA species of the present invention or a functional fragment thereof, or a nucleic acid molecule antisense thereto, or an antagomir or antibody which specifically binds miRNA, or a compound which modulates transcription of DNA encoding one or more of the miRNA species defined herein may be administered by any means and may be administered in combination with one or more other therapeutic agents and includes simultaneous (concurrent) and consecutive administration in any order of the miRNA species and other therapeutic agent(s).

The other therapeutic agent(s) used will depend upon the disease or disorder to be treated or prevented. However, for example where the disease is a glioma, suitable other therapeutic agents include erlotinib (Tarecva), or gefitinib (Iressa or ZD1839), 17-AAG (Hsp90 inhibitor), ZD6474, and sorafienib (Nexavar). Alternatively or in addition, the miRNA may be administered simultaneously and/or consecutively in any order with an agent which counters the side effects of miRNA.

The miRNA species of the present invention or a functional fragment thereof, or a nucleic acid molecule antisense thereto, or an antagomir or antibody which specifically binds miRNA, or a compound which modulates transcription of DNA encoding one or more of the miRNA species defined herein may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The miRNA species or a functional fragment thereof, or a nucleic acid molecule antisense thereto, or an antagomir or antibody which specifically binds miRNA, or a molecule which modulates transcription of DNA encoding miRNA may be administered to a subject periodically or repeatedly, and may be administered in the form of a pharmaceutical composition.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA. The carrier will depend on the route of administration, and again the person skilled in the art will readily be able to determine the most suitable formulation for each particular case.

The composition may be in any form suitable for its desired use. For example, depending upon the disease or disorder the composition may be in the form of a lotion, suspension, solution, spray, emulsion, gel, hair tonic, shampoo, jelly, suppository or retention enema, pessary, tampon, paste, foam, eyewash, drench, ointment, liquid soap, cream, solid soap, mouthwash, pastille or lozenge. The person skilled in the art will be readily able to formulate the composition so that it is in a form suitable for its intended use.

Administration of the miRNA species or a functional fragment thereof, or a nucleic acid molecule antisense thereto, or an antagomir or antibody which specifically binds miRNA species, or a compound which modulates transcription of DNA encoding one or more of the miRNA species of the present invention may treat or prevent a disease or disorder of a subject associated with an abnormal level of expression of EGFR. As used herein the terms "treating" and "preventing" mean any treatment of prevention of a disease or disorder in a subject by administering miRNA to the subject. "Treatment" and "prevention" includes: (a) inhibiting the disease or disorder, i.e., arresting its development; or (b) relieving or ameliorating the symptoms of the disease or disorder, i.e., cause regression of the symptoms of the disease or disorder. The effect may be therapeutic in terms of a partial or complete cure of the disease or disorder.

In some embodiments the miRNA or a functional fragment thereof, or a nucleic acid molecule antisense thereto, or an antagomir or antibody which specifically binds the miRNA and/or a compound which modulates transcription of DNA encoding one or more of the miRNA species as defined herein, may be used in the diagnosis of a disease or disorder associated with an abnormal level of expression of EGFR. The term "diagnosis" means the process of identifying a disease or disorder by its symptoms, via laboratory tests (including genotypic tests) or through physical findings. In some embodiments, the identification of, for example, miR-7 in a sample from a subject can be used in the diagnosis of a disease associated with the miRNA.

In some embodiments the miRNA species of the present invention, or a functional fragment thereof, or a nucleic acid molecule antisense thereto, or an antagomir or antibody which specifically binds the miRNA, and/or a compound which modulates transcription of DNA encoding one or more of the miRNA species defined herein, may be used to determine the prognosis of a disease or disorder associated with an abnormal level of expression of EGFR.

The term "prognosis" shall be taken to mean an indicator of the likelihood of progression of a disease or disorder diagnosed in a subject or the likelihood of a subject developing the disease or disorder. For example, depending upon the level of expression of miR-7, a subject might be identified as likely to develop a particular disease or disorder.

"Disease" as used herein is a general term used to refer to any departure from health in which a subject suffers and which is associated with an abnormal level of expression of EGFR. A "disorder" refers to an abnormal functioning of a function or part of the body of a subject and which is associated with an abnormal level of expression of EGFR.

The disease or disorder may be any disease or disorder associated with an abnormal level of expression of EGFR, such as a cancer, renal disease, pulmonary disease, cardiac disease, skin disease or infection (such as by a virus).

The term "cancer" as used herein refers to any malignant cell growth or tumour caused by abnormal and uncontrolled cell division. Any cancer may be treated, prevented, or diagnosed using a method of the invention as miRNA molecules are associated with cancer cells.

Examples of cancer include, but are not limited to, small-cell lung cancer, non-small cell lung cancer, gastrointestinal cancer, glioblastoma, cervical cancer, ovarian cancer, bladder cancer, breast cancer, colon cancer, colorectal cancer, endometrial carcinoma, oesophageal cancer, and various types of head and neck cancer. The preferred cancers for treatment according to some embodiments of the invention are glioma, breast, colon, lung, and prostate cancer.

The subject being treated according to some embodiments of the invention may be a subject of any species of mammalian animal, as miRNAs are found in numerous species of animal. For example, hundreds of miRNAs have been identified in mice and humans.

In some embodiments the subject is a human or a mammal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels) and horses. The term does not denote a particular age. Thus, both adult and newborn subjects are intended to be covered.

In some embodiments, compounds that are capable of modulating transcription of DNA encoding one or more of the miRNA species or affecting the endogenous expression and/or activity levels of one or more of the miRNA species as defined herein can be obtained by screening techniques.

Thus, the present invention provides screening methodologies useful in the identification of proteins and other compounds which bind to, or otherwise directly interact with, the miRNA species of the present invention. Screening methodologies are well known in the art (see eg., PCT International Publication No. WO 96/34099, published Oct. 31, 1996, which is incorporated by reference herein in its entirety). The proteins and compounds include endogenous cellular components which interact with the miRNA species in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the miRNA species defined herein.

Alternatively, any of a variety of exogenous compounds, both naturally occurring and/or synthetic (e.g., libraries of small molecules or peptides), may be screened for binding capacity. All of these methods comprise the step of contacting nucleic acid encoding the 3'-UTR of EGFR or like molecule eg SEQ ID NO:1-11 as defined herein or a cell expressing same with test compounds, allowing time for any binding or reaction to occur, and assaying for any bound complexes or activity.

The screening assays of the present invention also encompass high-throughput screens and assays to identify compounds capable of modulating the expression and/or activity of the miRNA species of the present invention. In accordance with this embodiment, the systems described below may be formulated into kits. To this end, cells expressing constructs encoding, for example, one of the nucleic acid molecules disclosed in SEQ ID NO:1 to 11 operably linked to a reporter molecule can be packaged in a variety of containers, e.g., vials, tubes, microtitre well plates, bottles, and the like. Other reagents can be included in separate containers and provided with the kit; e.g., positive control samples, negative control samples, buffers, cell culture media, etc.

In some embodiments, agents of the present invention that are capable of regulating the endogenous levels of miRNA species and/or their activity can be initially identified using in vitro cell based assays. For example, a system such as Chroma-Luc™, Luc™ or GFP™ reporter genes can be provided in multiple different cloning vector formats. The Basic vector versions are general-purpose reporter vectors based on the design, for example of the pGL3-Basic Vector, allowing cloning of the 3'-UTR coding sequence e.g. SEQ ID NO:1 to 11 at the 5' end of the reporter gene. Expression of luciferase, or any reporter gene, activity in cells transfected with this "pGL3-Promoter Vector" depends compounds being able to induce directly or indirectly the expression of the reporter. In addition to the basic vector configuration, other systems such as the Chroma-Luc™ genes are available in a vector configuration containing an SV40 promoter and SV40 enhancer, similar to the pGL3-Control Vector. The presence of the SV4.0 promoter and enhancer sequences result in strong expression of luc+ in many types of mammalian cells. Thus this technology and any other vector modification is suitable for rapid quantitation in multiwell plates and in high-throughput applications to assay for compounds which are potentially capable of modifying the miRNA expression by measuring the reporter gene downstream. These identified compounds can than be tested in cells. In general, any luminometer capable of measuring filtered luminescence should be able to perform dual-colour assays and any scientist skilled in the art can reproduce these assays.

The invention will now be further described by way of reference only to the following non-limiting examples. It should be understood, however, that the examples following are illustrative only, and should not be taken in any way as a restriction on the generality of the invention described above.

EXAMPLE 1

Specificity of miRNA Species miR-7 for EGFR in Cell Lines which Over-Express EGFR EGFR is over expressed in numerous cancers, including glioblastoma, lung cancer, and breast cancer. Accordingly, we aimed to show that one of the miRNA species disclosed herein (miR-7) was specific for EGFR in glioblastoma, lung cancer, and breast cancer cell lines, and therefore could modulate the level of expression of EGFR, and that miR-7 could be used in the management of cancers including glioblastoma, lung cancer, and breast cancer.

Figure 2:
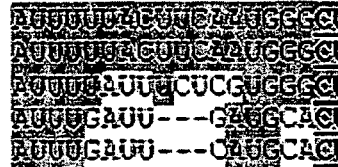
FIG. 2 shows the sequence alignment of putative miR-7 targets in EGFR mRNA 3'-UTR shows that sites A, B, C are not conserved between human, mouse and rat. The miR-7 seed target sequence (UCUUCC) is shown in bold and underlined, and conserved nucleotides are shaded. The miR-7 target A sequences of *H. sapiens, P. troglodytes, C. familiaris, M musculus, R. norvegius* used for the alignment correspond to SEQ ID NO's: 65, 66, 67, 68 and 69 respectively. Gaps in the *M. musculus* and *R. Norvegius* sequences introduced by the alignment are represented in the figure by dashed lines. The miR-7 target B sequences of *H. sapiens, P. troglodytes, C. familiaris, M musculus, R. norvegius* used in the alignment correspond to SEQ ID NO's: 70, 71, 72, 73 and 74 respectively. Gaps in the *C. familiaris, M. musculus,* and *R. norvegius* sequences introduced by the alignment are shown as dashed lines. The miR-7 target C sequences of *H. sapiens, P. troglodytes, C. familiaris, M musculus, R. norvegius* used in the alignment correspond to SEQ ID NO's: 75, 76, 77, 78 and 79 respectively. Gaps in the *C. familiaris* sequence introduced by the alignment are shown as dashed lines.

In view of the finding that EGFR expression is regulated in part via cis-acting 3'-UTR mRNA stability sequences, we sought to identify miRNAs that could regulate EGFR gene expression in human cells. Using TargetScan (Lewis et al., 2005, Cell, 120, 15) three putative miR-7 target sites were identified (A, B, C; FIG. 1). The 3' end of each site contained the hexamer motif UCUUCC complementary to the seed region (nt. 2-7) at the 5' end of human miR-7 (hsa-miR-7) (FIG. 2). While miR-7 is normally expressed in the brain, lens, pituitary and hypothalamus, its expression is significantly decreased in pituitary adenomas and in a panel of CNS cancer cell lines relative to normal CNS tissue, suggesting that it may function as a tumor suppressor in these systems by inhibiting oncogene expression. Interestingly, the EGFR 3'-UTR is poorly conserved across species with sequence differences in each of the three putative miR-7 target sites between human, mouse and rat (FIG. 2). Binding sites that are not conserved between species are often ignored in an attempt to reduce the number of false positives in target prediction sets. However, the evolution of miRNAs and their target mRNAs suggests that this exclusion could also increase the rate of false negative predictions. In mice, miR-7b regulates translation of the Fos oncogene via a 3'-UTR target site that is not present in human Fos mRNA.

Figure 3:
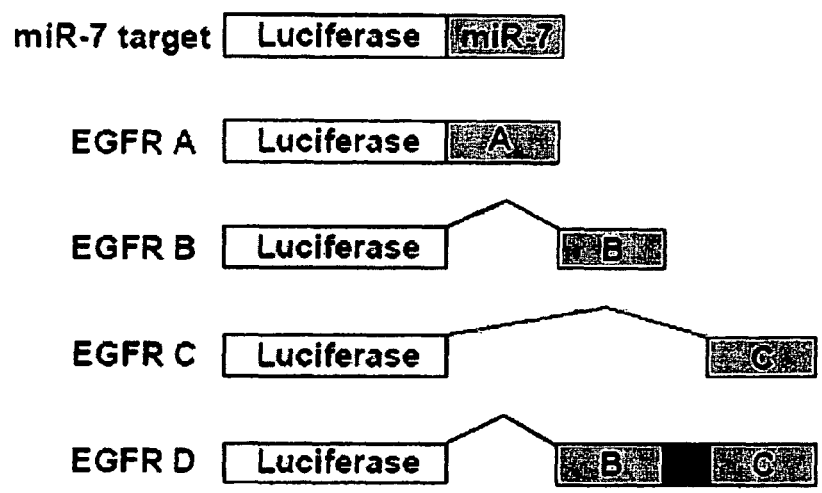
FIG. 3 shows a schematic representation of luciferase reporter constructs for consensus miR-7 target and EGFR 3'-UTR miR-7 target sites.

To investigate the putative interaction between miR-7 and its predicted EGFR mRNA 3'-UTR target sites, we first generated reporter vectors containing miRNA target sequences downstream of the luciferase ORF (FIG. 3). pGL3-miR-7-report was generated by ligating annealed DNA oligonucleotides corresponding to a perfect hsa-miR-7 target site (5'-CAA CAA AAT CAC TAG TCT TCC A-3' (SEQ ID NO:55) and 5'-TGG AAG ACT AGT GAT TTT GTT G-3' (SEQ ID NO:56) to unique SpeI and ApaI sites that were inserted 3' of the luciferase ORF of pGL3-control (Promega) firefly luciferase reporter vector (designated pGL3-control-MCS; Giles, et al., 2003, J. Biol. Chem., 278, 2937). Wild type (WT) EGFR target reporter plasmids pGL3-EGFR-A, -B, and -C were generated by cloning annealed oligonucleotides corresponding to nt. 4214-4260, nt. 4302-4348, and nt. 4585-4631, respectively, of EGFR (GenBank accession number NM_005228) mRNA 3'-UTR into SpeI and ApaI sites in pGL3-control-MCS. Plasmid pGL3-EGFR-D contained a PCR-generated EGFR 3'-UTR sequence that spanned the predicted miR-7 target sites B and C. Mutant (MT) reporters were also generated that included three nucleotide substitutions to impair binding of the miR-7 seed sequence to its target. Plasmids pGL3-RAF1-WT and pGL3-RAF1-MT were constructed by cloning annealed DNA oligonucleotides corresponding to nt. 2965-3030 of the Raf1 mRNA 3'-UTR (GenBank accession number NM_002880) into the SpeI and ApaI sites in pGL3-control-MCS. The sequence of all plasmids was confirmed by sequencing.

A target site with perfect complementarity to the miR-7 sequence, EGFR 3'-UTR sequences (A, B, C, D) with predicted miR-7 target sites, and these same sequences with three point mutations in the seed match region predicted to disrupt miR-7 binding (FIG. 4). A549, MDA-MB-468, U87MG, U251MG and HeLa cell lines were obtained from the American Type Culture Collection (ATCC) and cultured at 37° C. in 5% $CO_2$ with DMEM supplemented with 10% fetal bovine serum and 1% penicillin/streptomycin. Synthetic miRNA precursor molecules corresponding to human miR-7 (Pre-miR miRNA Precursor Product ID: PM10568; Anti-miR miRNA Inhibitor Product ID: AM10568) and a negative control miRNA (miR-NC; Pre-miR miRNA Precursor Negative Control #1, Product ID: AM17110; Anti-miR miRNA Inhibitor Negative Control #1, Product ID: AM17010) were obtained from Ambion. Cells were seeded 24 h prior to transfection in 6-well plates or 10 cm dishes and transfected using Lipofectamine 2000 (Invitrogen) with miRNA precursors (Ambion) at final concentrations ranging from 0.1-30 nM. Cells were harvested at 12-24 h (for RNA extraction) or 3 d (for protein extraction). For reporter assays, cells were seeded in 24-well plates and transfected using Lipofectamine 2000 (Invitrogen) with 100 ng of pGL3-control firefly luciferase reporter DNA and 5 ng of pRL-CMV renilla luciferase reporter DNA as a transfection control. Lysates were assayed for firefly and renilla luciferase activities 24 h after transfection using the Dual Luciferase Report Assay System (Promega) and a Fluostar OPTIMA microplate reader (BMG Labtech). Expression values were normalized to renilla luciferase and expressed relative to the average value for each miR-NC-transfected wild type reporter construct.

Figure 5:
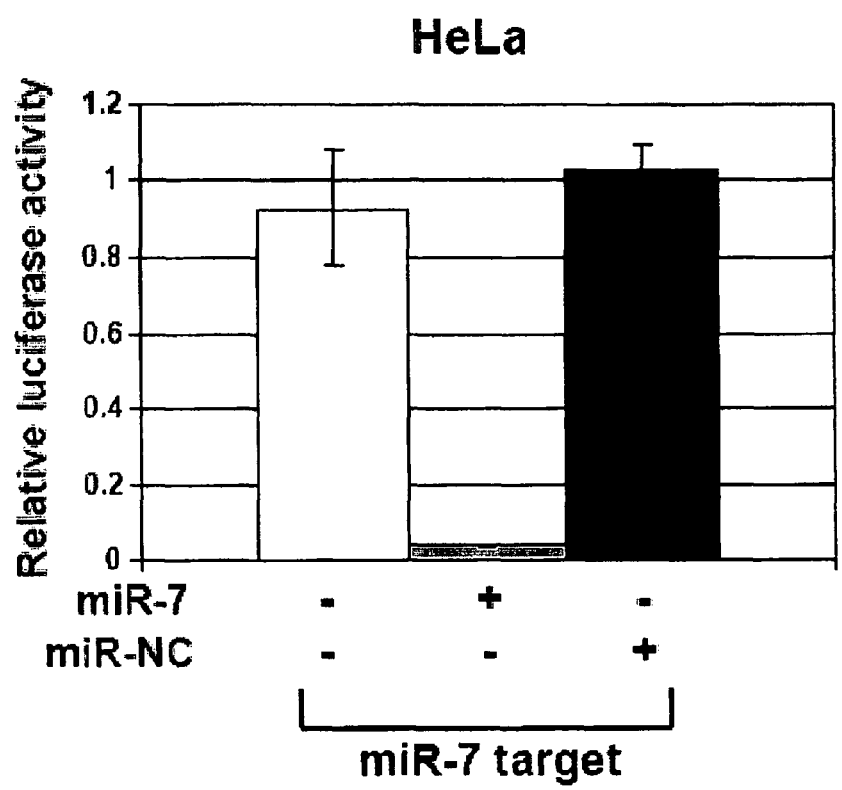
FIG. 5 shows HeLa cells that were transfected with consensus miR-7 target 3'-UTR luciferase construct and miR-7 or miR-NC precursor. Relative luciferase expression (firefly normalized to renilla) values are expressed as a ratio of reporter vector only (±SD).

In FIG. 4 it can be seen that HeLa cells transfected with synthetic miR-7 precursor, expression of the perfect target reporter was reduced, an effect that was not evident with a negative control miRNA precursor (miR-NC) (FIG. 5).

Figure 6:
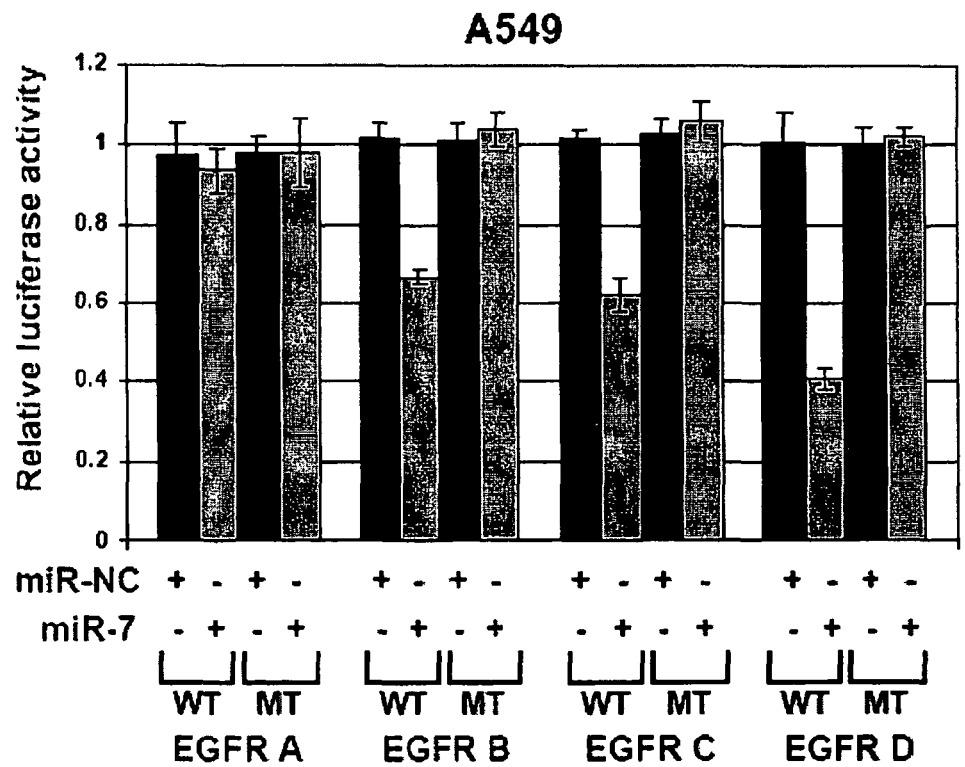
FIG. 6 shows A549 cells that were transfected with WT or MT EGFR target site A, B, C or D 3'-UTR reporter along with miR-7 or miR-NC precursor. Relative luciferase expression (firefly normalized to renilla) values are the ratio of miR-7-treated reporter vector compared to miR-NC-treated reporter vector (±SD).

Transfection studies using human NSCLC cells (A549, which overexpress EGFRs) examined the relative contribution of each putative miR-7 target site in the EGFR 3'-UTR to the regulation of target gene expression. We found that expression of miR-7 reduced reporter expression via target sites B and C compared to miR-NC, while the corresponding mutant reporters were not affected (FIG. 6). In contrast, miR-7 had no effect on reporter gene expression mediated by the EGFR 3'-UTR target site A (FIG. 6), despite this site being a predicted target for miR-7 binding. This suggested that target site A alone was not a target for miR-7 binding. Interestingly, the presence of target sites B and C (plasmid construct EGFR D, FIG. 3) in the same reporter construct conferred additive, but not synergistic, repression with miR-7 that was not observed with the EGFR D mutant reporter (FIG. 6). Together, these data indicate that two of the three predicted miR-7-binding sites in the EGFR mRNA 3'-UTR are likely to be specific targets for miR-7, and furthermore suggest that target sites B and C may act in an additive fashion to amplify the repression of EGFR expression by miR-7.

EXAMPLE 2

The Effect of miR-7 on EGFR mRNA and Protein Expression in Cell Lines

Next, we sought to determine the effect of miR-7 on EGFR mRNA and protein expression in A549 and EGFR-overexpressing MDA-MB-468 breast cancer cells. Total RNA was extracted from cell lines with Trizol reagent (Invitrogen) and RNeasy columns (Qiagen) and treated with DNase I (Promega) to eliminate contaminating genomic DNA. For semi-quantitative measurement of EGFR and β-actin transcript expression, 1 µg of RNA was reverse transcribed to cDNA using random hexamers and AMV reverse transcriptase (Promega). PCR primers for EGFR and β-actin are: EGFR-F, 5'-CAC CGA CTA GCC AGG AAG TA-3' (SEQ ID NO:57); EGFR-R, 5'-AAG CTT CTT CCT TGT TGG AAG AGC CCA TTGA-3' (SEQ ID NO:58); β-actin-F, 5'-GCC AAC ACA GTG CTG TCTGG-3' (SEQ ID NO:59); β-actin-R, 5'-TAC TCC TGC TTG CTG ATC CA-3' (SEQ ID NO:60). For qRT-PCR, 1 µg of RNA was reverse transcribed with random hexamers and Thermoscript (Invitrogen). Real-time PCR for Raf1 and GAPDH was performed using a Corbett 3000 RotorGene instrument (Corbett Research) with QuantiTect SYBR Green PCR mixture (Qiagen) with primers that were obtained from PrimerBank Wang & Seed, 2003, Nucleic Acids Res., 31, 154): RAF1-F, 5'-GCA CTG TAGCAC CAA AGT ACC-3' (SEQ ID NO:61); RAF1-R, 5'-CTG GGA CTC-CAC TAT CAC CAA TA-3' (SEQ ID NO:62); GAPDH-F, 5'-ATG GGG AAG GTG AAG GTC G-3' (SEQ ID NO:63); GAPDH-R, GGG GTC ATTGAT GGC AAC AAT A-3' (SEQ ID NO:64). Expression of Raf1 mRNA relative to GAPDH mRNA was determined using the $2^{-\Delta\Delta C_T}$ method (Livak & Schmittgen, 2001, Methods, 25, 402).

Cytoplasmic protein extracts were prepared as described (Thomson et al., 1999, Biotechniques, 27, 1032), resolved on NuPAGE 4-12% Bis Tris gels (Invitrogen) and transferred to PVDF (Roche). Membranes were probed with anti-EGFR mouse monoclonal antibody (1:1000, Neomarkers Cat# MS-400-P1), anti-Raf-1 mouse monoclonal antibody (1:1000, Santa Cruz sc-7267), or anti-β-actin mouse monoclonal antibody (1:10,000, Abcam ab6276-100), prior to detection with ECL Plus detection reagent (General Electric Healthcare) and ECL-Hyperfilm (General Electric Healthcare).

Transfection of miR-7 precursor, but not miR-NC precursor, induced a significant reduction in EGFR mRNA expression in A549 cells observed at 12 h post-transfection (FIG. 7A), consistent with miR-7 promoting EGFR mRNA decay. This effect is in contrast to the results of a study in which miR-7 regulates translation of Fos mRNA in the mouse hypothalamus, suggesting that miR-7 is able to regulate either the stability and/or translation of target mRNAs.

Furthermore, when compared with miR-NC, at 72 h post-transfection with miR-7 there was a dramatic reduction in EGFR protein expression in A549 and MDA-MB-468 cells (FIG. 7B), even at low concentrations of miR-7 precursor.

Cells were cultured and transfected on coverslips in 6 well plates, fixed in ice cold methanol and blocked with 1% BSA/PBS, followed by incubation with EGFR antibody (1:500, Neomarkers Cat# MS-378-P1). After washing, cells were incubated with secondary antibody (1:1000, Alexa Fluor 488 goat anti-mouse IgG, Invitrogen Cat# A11029), with Hoechst dye (1:10,000, Hoechst AG) and coverslips mounted and stained cells analyzed and photographed with fluorescence microscopy (Olympus IX71S1F-2 microscope) using identical exposures.

Similarly, EGFR protein expression was observed to be reduced by miR-7 transfection in EGFR-positive U87MG glioblastoma cells by immunofluorescence and immunoblotting. The latter result was particularly intriguing given the reported downregulation of miR-7 expression and the established role for EGFR overexpression in CNS tumors.

EXAMPLE 3 miR-7 Inhibits Cell Cycle Progression and Induces Cell Death of Breast and Lung Cancer Cells In order to study the effects of miR-7 on cell cycle arrest cells were trypsinized, permeabilized, stained with propidium iodide and analysed on a Coulter EPICS XL-MCL (Coulter Corp. flow cytometer. Cell cycle analysis was performed using MultiPlus AV MultiParameter data analysis software (Phoenix Flow Systems).

Cells were plated in 6 cm dishes in 6 mL of Dulbecco's Eagle Media plus 5% fetal bovine serum, 24 hours prior to transfection. A549 cells were plated at 300,000/well. MDA-468 cells were plated at 800,000/well. Immediately prior to transfection, the media was replaced with 6 mL of fresh media. Cells were transfected using Lipofectamine 2000 reagent. For each condition, a stock transfection mix was prepared with 22.5 µL of 10 µM miRNA precursor (Ambion catalogue no. 17110 pre-mir negative control #1) and 727.5 µL of OptiMEM I Media for each dish to be transfected, for a final precursor concentration of 30 nM. A stock solution of Lipofectamine 2000 diluted in OptiMEM I Media was also prepared, with 45 µL of Lipofectamine 2000 and 705 µL of OptiMEM I Media for each well to be transfected. Solutions were incubated at room temperature for 5 minutes. Diluted Lipofectamine stock was then added to each condition tube at a ratio of 1:1 and gently pipetted up and down. Solutions were incubated at room temperature for 20 minutes. 1.5 mL of transfection mix was added to each well. Plates were rocked gently back and forth. The media was replaced with 6 mL of fresh media 4 hours after transfection.

Figure 8:
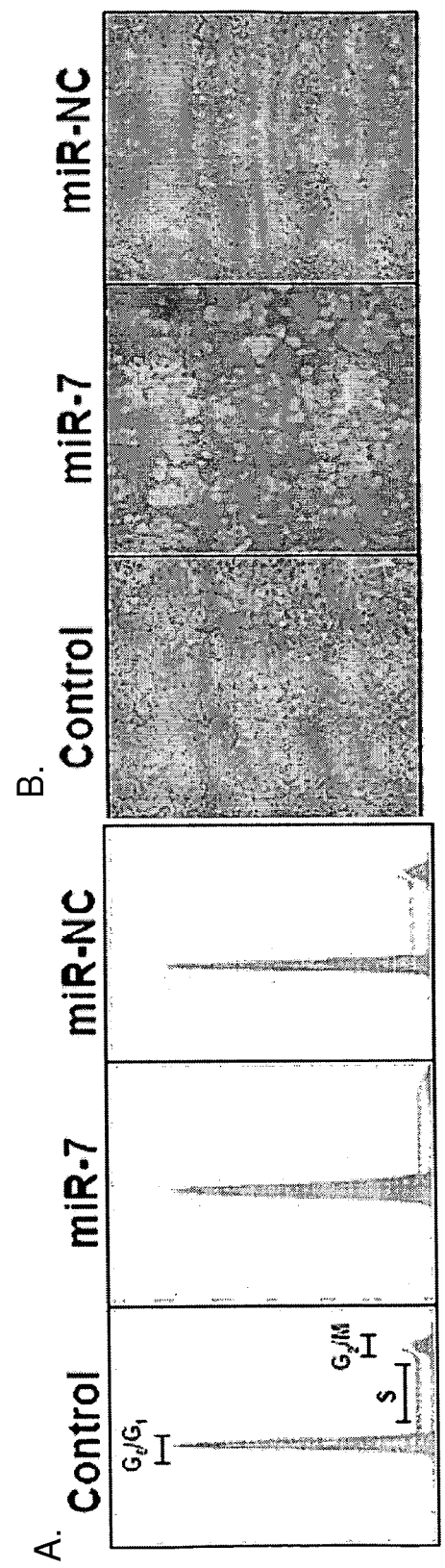
FIG. 8 shows the results of cell cycle analysis of A549 lung cancer cells treated with miR-7 or nonsense miRNA (miR-NS). Panel A show the results of cell cycle analysis of A549 lung cancer cells treated with miR-7 or nonsense miRNA (miR-NS). Panel B shows the same cells analysed by light microscopy showing miR-7 induces widespread cell death.

Transfection of A549 cells with miR-7 precursor induced cell cycle arrest at $G_1$ (FIG. 8A), and caused a significant decrease in A549 cell viability compared with vehicle and miR-NC transfected A549 cells (FIG. 8B). However, cell death induced by miR-7 precursor transfection did not appear to involve apoptosis, due to the absence of (a) an apoptotic, sub-$G_1$ cell population by propidium iodide staining and flow cytometry (FIG. 8A), and (b) activation of the executioner caspases 3 and 7 (data not shown). Thus, it is likely that miR-7 expression induces a broad program of gene expression that reduces A549 cell viability through necrosis.

In view of the evidence that miRNAs can have multiple, functionally-related targets, we performed microarray analysis to identify miR-7 target genes and functional trends using RNA samples from A549 cells treated with miR-7 or miR-NC. Total RNA was isolated from A549 cells transfected with miR-7 or miR-NC using Trizol reagent (Invitrogen) and RNeasy columns (Qiagen) and assessed using a 2100 Bioanalyzer (Agilent Technologies). Gene expression profiling was performed by microarray hybridization to Human Genome U133 Plus 2.0 array chips (Affymetrix). Gene expression data was analyzed using GeneSifter software (VizX Labs). Data comparisons were from two experimental replicates. Those genes with a p<0.05 and that were >2.0-fold significantly downregulated by miR-7 transfection were selected for further analysis on the basis that they could represent direct miR-7 targets. MiR-7 target predictions were performed using miR-Target (Wang & Wang, 2006, *Nucleic Acids Res.*, 34, 1646), miRanda (Enright et al., 2003, *Genome Biol.*, 5, 1), PicTar (Krek et al., 2005, *Nat. Genet.*, 37, 495) and TargetScan software (Lewis et al., 2003, *Cell.*, 115, 787). Microarray expression data will be deposited in Gene Expression Omnibus (GEO) and provided with an Accession Number.

Figure 7:
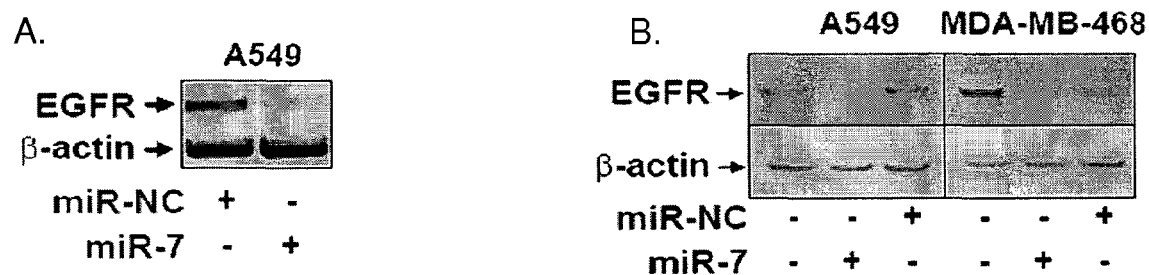
FIG. 7 shows miR-7 regulates EGFR expression and alters cell cycle progression and viability of A549 NSCLC cells. Panel A shows A549 cells were transfected with miR-7 or miR-NC precursor and RNA isolated at 12 h for semi-quantitative RT-PCR analysis of EGFR and β-actin mRNA expression. Panel B shows EGFR and β-actin immunoblot using 15 µg of cytoplasmic protein extracts from A549 and MDA-MB-468 cells transfected with miR-7 or miR-NC for 3 d.
Figure 9:
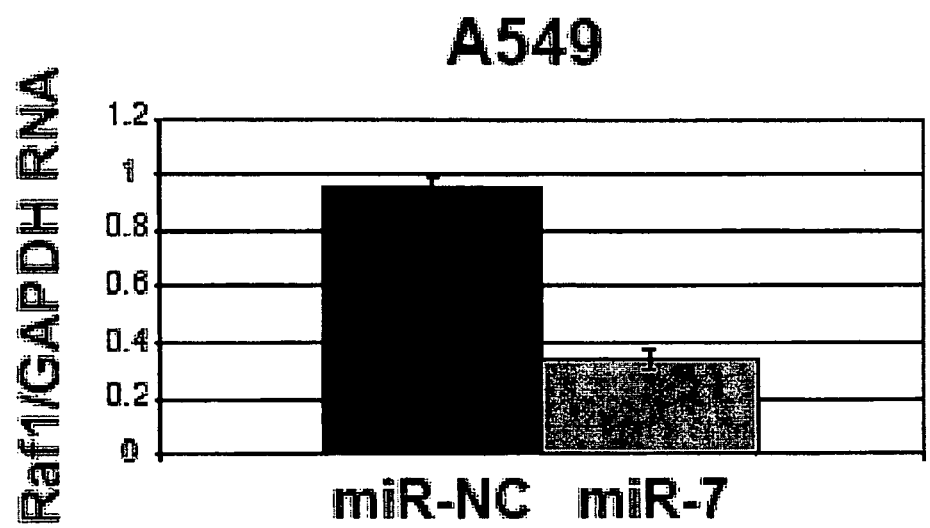
FIG. 9 shows that miR-7 regulates Raf1 expression via specific binding to the Raf1 mRNA 3'-UTR. qRT-PCR validation of Raf1 mRNA expression following transfection of A549 cells for 24 h with miR-7 or miR-NC. Values are fold-change (SD) in Raf1 mRNA expression relative to GAPDH mRNA expression between triplicate miR-NC and miR-7 samples.
Figure 10:
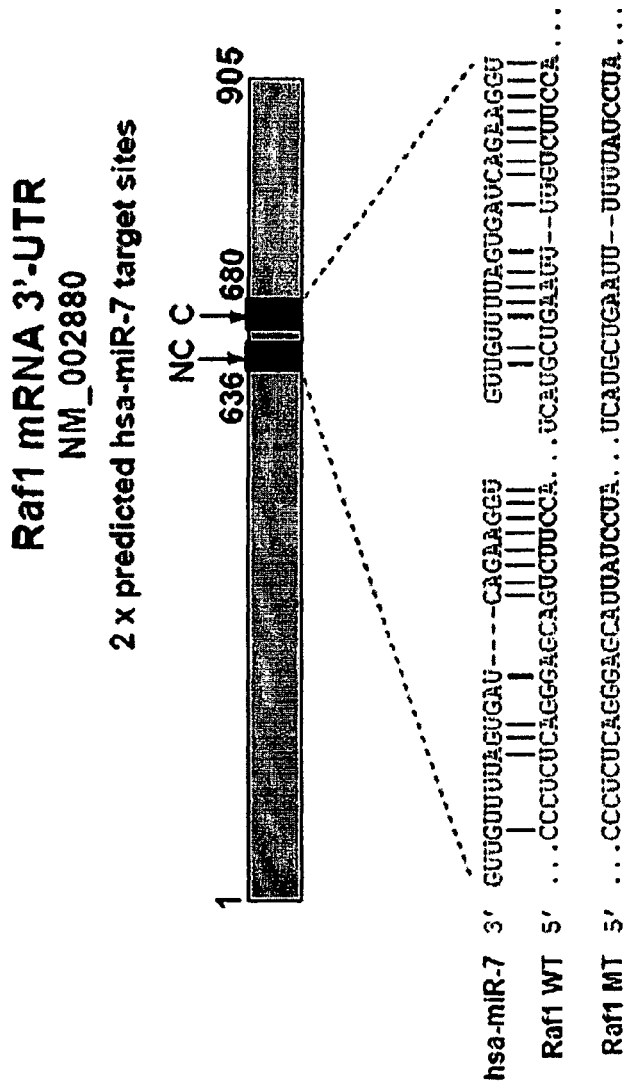
FIG. 10 shows Raf1 mRNA 3'-UTR contains conserved (C) and non-conserved (NC) seed target sites for miR-7 binding. The hsa-miR-7 sequence used in the illustrated sequence alignment corresponds to SEQ ID NO: 80. The 5' end of the Raf 1 WT sequence illustrated in the alignment corresponds to SEQ ID NO: 87 and the 3' end of that sequence corresponds to SEQ ID NO: 88. The 5' end of the Raf 1 MT sequence illustrated in the alignment corresponds to SEQ ID NO: 89 and the 3' end of that sequence corresponds to SEQ ID NO: 90. Gaps in each of the sequences introduced by the alignment are shown as dashed lines.

In miR-7-transfected A549 cells, 248 transcripts were significantly downregulated and 199 transcripts were significantly upregulated by at least 2-fold (p<0.05) when compared to miR-NC-transfected A549 cells. Furthermore, there was significant enrichment (2.18-fold, p=0.025) for predicted miR-7 target genes, but not for predicted target genes of any other miRNA, among the recognised set of 248 downregulated genes. The enrichment for putative miR-7 target genes among the genes downregulated in miR-7-transfected A549 cells is consistent with other studies that identified miRNA target genes by microarray analysis. EGFR was significantly downregulated by miR-7 for all three microarray chip probes (3.13-, 3.07-, and 2.87-fold), consistent with the observed reduction in EGFR mRNA expression with miR-7 transfection (FIG. 7A). Interestingly, Raf1, a member of the EGFR-Ras-Raf-MEK-ERK signaling cascade, was also downregulated by miR-7 (3.47-fold). This result was confirmed by qRT-PCR in A549 cells treated with miR-7 or miR-NC precursor (FIG. 9), suggesting that miR-7 promotes degradation of Raf1 mRNA. TargetScan analysis revealed that the human Raf1 3'-UTR contains two predicted miR-7 target sites (one conserved, one non-conserved; FIG. 10).

EXAMPLE 4 miR-7 Regulates RAF-1 Protein Expression in Cancer Cell Lines Via a Target Site in the 3'-Untranslated Region of RAF-1 mRNA The effects of miR-7 expression on Raf-1 gene expression were determined in MDA-468 (breast cancer cell line) and A549 (lung cancer cell line) cells. Raf-1 is an established downstream effector of EGFR via the Raf-MEK-ERK pathway which is considered a therapeutic target in cancer (eg. this pathway is a target for Nexavar).

A549 lung cancer or MDA-468 breast cancer cells were plated in 6-well plates at 100,000/well or 300,000/well, respectively, in 2 mL of Dulbecco's Modified Eagle Media (DMEM) plus 5% fetal bovine serum, 24 hours prior to transfection. Immediately prior to transfection, the media was replaced with 2 mL of fresh media. Cells were transfected using Lipofectamine 2000 reagent. For each transfection condition, a stock mix was prepared with 7.5 µl of 10 µM miRNA precursor RNA (Ambion Catalogue No. 17110 pre-mir negative control #1 or Ambion Catalogue No. 17100 ID265 pre-mir hsa-miR-7) and 242.5 µL of OptiMEM I Media for each well to be transfected, for a final precursor concentration of 30 nM. A stock solution of Lipofectamine 2000 diluted in OptiMEM I Media was also prepared, with 15 µL of Lipofectamine 2000 and 235 µL of OptiMEM I media for each well to be transfected. Solutions were incubated at room temperature for 5 minutes. Diluted Lipofectamine tock was then added to each condition tube at a ratio of 1:1 and gently pipetted up and down.

Solutions were incubated at room temperature for 20 minutes. 500 µL of transfection mix was added to each well. Plates were gently rocked back and forth. The media was replaced with 2 mL of fresh media 4 hours after transfection.

Figure 12:
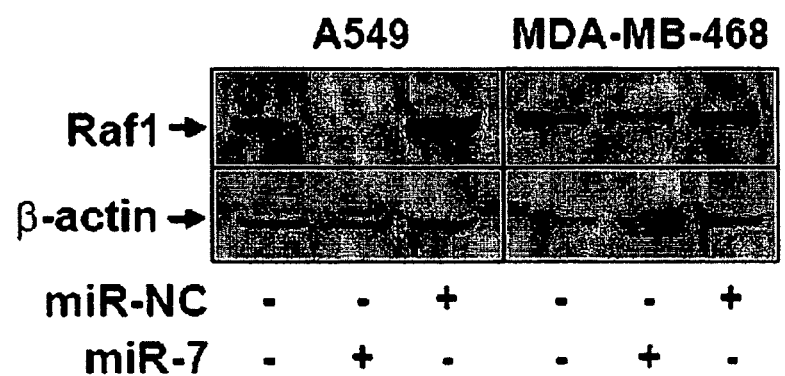
FIG. 12 shows a graph of the effect of precursor mir-7 or control RNA on pGL3-Raf-1 in A549 cells.

As shown in FIG. 12, in cells transfected with miR-7 precursor there was a significant reduction in Raf-1 protein expression by immunoblotting in A549 and MDA-468 cell lines. Lanes 1 and 4 show Raf-1 and beta-actin protein expression in A549 and MDA-468 cells, respectively, that were treated with transfection reagent only (ie. Lipofectamine 2000 only). Lanes 2 and 5 show Raf-1 and beta-actin protein expression in A549 and MDA-468 cells, respectively, that were treated with miR-7 precursor (30 nM) for 3 days. Lanes 3 and 6 show Raf-1 and beta-actin protein expression in A549 and MDA-468 cells, respectively, that were treated with a negative control (NC) miRNA precursor (30 nM) for 3 days.

To determine whether Raf-1 represented a specific target of miR-7 in cancer cells, A549 cells were transfected with 0.5 nM, 1 nM or 10 nM precursor miR-7 (Ambion Catalogue No. 17100 ID265 pre-mir hsa-miR-7) or pre-mir negative control #1 (Ambion Catalogue No. 17110 pre-mir negative control #1) along with a luciferase reporter plasmid carrying the wild type Raf-1 3'-UTR target region for miR-7 or a mutated version of this target region, and a renilla luciferase plasmid for normalisation of transfection efficiency.

The transfected cell lines were assayed for firefly and renilla luciferase activity using the Dual Luciferase Reporter Assay Kit (Promega) following the manufacturer's instructions. Data for firefly luciferase was normalised to renilla luciferase to give a relative luciferase activity.

Figure 11:
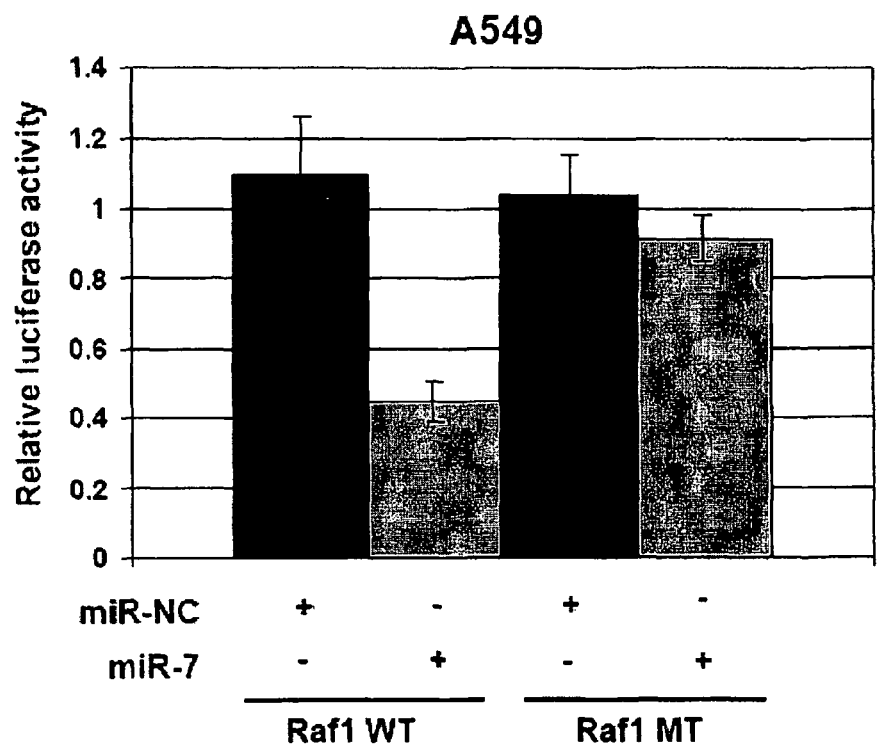
FIG. 11 shows A549 cells transfected with WT or MT luciferase-Raf1 3'-UTR reporter vector and either miR-7 or miR-NC. Values are relative luciferase expression (firefly normalized to renilla) as a ratio of miR-NC-transfected cells (±SD).

As shown in FIG. 11, the Raf-1 3'-UTR contains a specific target site for miR-7, but not the negative control miRNA in A549 NSCLC cells (FIG. 12). Lanes 1-3 of FIG. 12 represent the wild-type 3'-UTR Raf-1 mRNA sequence that is a target for miR-7, lanes 4-6 represent a mutated version of this sequence. Lanes 1 and 4 show normalised luciferase activity for A549 cells that were transfected with the wild-type or mutant miR-7 target sequence, respectively, from Raf-1. Lanes 2 and 5 demonstrate specificity of miR-7 for the Raf-1 target site. The data show normalised luciferase activity for A549 cells that were transfected with the wild-type or mutant miR-7 target sequence (lanes 2 and 5, respectively), from Raf-1, together with miR-7 precursor for 24 hours. Luciferase activity is repressed in lane 2, ie. in the presence of both the wild-type Raf-1 target site luciferase reporter and miR-7, but not in lane 5, ie. in the presence of the mutant Raf-1 target site luciferase reporter and miR-7.

Lanes 3 and 6 demonstrate specificity of the Raf-1 target site for miR-7. The data show normalised luciferase activity for A549 cells that were transfected with the wild-type of mutant miR-7 target site (lanes 3 and 6, respectively), from Raf-1, together with the negative control miRNA precursor for 24 hours. Luciferase activity is repressed in neither instance, indicating a requirement for miR-7 to block luciferase expression via the wild-type Raf-1 target site.

Thus, in these transfection studies with A549 cells, miR-7 reduced reporter activity in cells transfected with a luciferase construct that carried a wild-type Raf1 miR-7 target sequence but not an analogous insert with three point mutations in the seed match region (FIG. 11). This indicated that the Raf1 mRNA 3'-UTR is a specific target for binding of miR-7. Furthermore, Raf1 protein expression was substantially decreased in A549 and MDA-MB-468 cells transfected with miR-7 precursor compared with miR-NC precursor. (FIG. 12). These data provide evidence that miR-7 directly regulates expression of Raf1, a downstream effector of EGFR signaling via the Raf-MEK-ERK MAPK cascade, that is commonly activated by mutations and/or overexpressed in human cancers.

EXAMPLE 5 miR-7 Regulates Expression of a Number of mRNAs that Contain Putative miR-7 Target Sites To identify novel targets of miR-7 activity in cancer cells, we performed microarray analysis of A549 NSCLC cells that were transfected with either 30 nM precursor miR-7 (Ambion Catalogue No. 17100 ID265 pre-mir hsa-miR-7) or pre-mir negative control #1 (Ambion Catalogue No. 17110 pre-mir negative control #1). Total RNA was isolated at 24 hours post-transfection using Trizol reagent (Invitrogen, Australia) and RNeasy RNA total purification columns (QIAGEN, Australia), according to manufacturer's instructions. RNA quality and integrity was confirmed with an Agilent Bioanalyser (Agilent Technologies, Inc., 5301 Stevens Creek Blvd, Santa Clara, Calif. 95051, United States). Labeled cDNA from each sample was hybridised to U133plus1 chips (Affymetrix, USA) and microarray data was analysed using Genesifter software (200 West Mercer Street, Suite 500, Seattle, Wash. 98119-3995 USA) and Microsoft Excel (Microsoft, Seattle, Wash., USA). A number (>40) of mRNAs that were significantly down-regulated over two independent experiments and contained predicted 3'-UTR mRNA target sites for miR-7 binding were selected for further analysis. Indicated in the table are the average fold change in the microarray studies (relative to negative control-treated samples), the official GenBank gene name, the LocusLink identifier and GeneID from the NCBI/GenBank database World Wide Web at ncbi.nlm.nih.gov and the number of instances for which the given gene was predicted to be a miR-7 target (using free, web-based prediction tools such as TargetScan, PicTar, miRanda together with an prediction algorithm developed in-house).

To investigate potential functional trends for miR-7 we examined Kyoto Encyclopedia of Genes and Genomes (KEGG) pathways for significant enrichment of genes that were downregulated in microarray analysis of A549 cells transfected with miR-7 precursor (FIG. 13), since these may include actual miR-7 targets. Investigation of the enrichment of gene sets for predicted miRNA targets was conducted using the L2L microarray analysis tool (Newman & Weiner, 2005, *Genome Biol.*, 6, 81). KEGG functional pathway analysis. Analysis of the enrichment of gene sets for functional KEGG pathways was performed using GeneSifter software (VizX Labs).

Notably, "Glioma", "ErbB signaling pathway", "GnRH signaling pathway", "Long-term potentiation" and "Gap junction" pathways were significantly enriched with genes that were downregulated by miR-7 transfection. These are consistent with a role for miR-7 in the regulation of EGFR signaling, and with the brain and pituitary-specific expression of miR-7 and its downregulation in CNS and pituitary tumors. In addition to the validated target genes EGFR and Raf1, several other downregulated genes in these pathways contain predicted binding sites for miR-7. These include genes involved in calcium signaling (CALM3 and CAMK2D, downregulated 7.1- and 2.08-fold, respectively), cytoskeleton reorganisation and nuclear signaling (PAK1, downregulated 2.2-fold), and cAMP synthesis and intracellular signaling (ADCY9, downregulated 3.38-fold).

The claims defining the invention are as follows:

1. A method for reducing the expression of epidermal growth factor receptor (EGFR) or a downstream effector molecule in a cell, comprising:
   a) selecting an miRNA capable of interacting with the sequence UCUUCC in the 3'-untranslated region (UTR) of the mRNA of said EGFR or of a downstream effector molecule selected from the group consisting of Raf-1, CALM3, CAMK2D, PAK1, and ADCY9; and
   b) contacting said cell with said miRNA under conditions whereby expression of EGFR in said cell is reduced.

2. The method of claim 1, wherein the 3'-UTR comprises a sequence which is encoded by a sequence having at least about 90% identity with at least one sequence selected from the group consisting of the sequences set forth in SEQ ID NOs:1-11.

3. The method of claim 1, wherein the 3'-UTR is encoded by a sequence contained within the sequence set forth in SEQ ID NO:1.

4. The method of claim 1, wherein said contacting comprises contacting said cell with an agent comprising a nucleic acid molecule encoding an miRNA precursor, wherein said precursor is processed in said cell to form said miRNA.

5. The method of claim 1, wherein the said miRNA is miR-7.

6. The method of claim 5, wherein the miR-7 is the sequence set forth in SEQ ID NO: 48.

7. The method of claim 1, wherein the miRNA comprises the sequence set fourth in SEQ ID NO: 52.

8. The method of claim 1, wherein the miRNA comprises a nucleic acid molecule having at least about 90% identity with the sequence set forth in SEQ ID NO: 48.

9. A method of inhibiting the growth or differentiation of a cell expressing EGFR or a downstream effector molecule, comprising:
   a) selecting an miRNA capable of interacting with the sequence UCUUCC in the 3'-untranslated region (UTR) of the mRNA of said EGFR or of a downstream effector molecule selected from the group consisting of Raf-1, CALM3, CAMK2D, PAK1, and ADCY9; and
   b) contacting said cell with said miRNA under conditions whereby growth or differentiation of said cell is inhibited.

10. The method of claim 9, wherein-said cell is a cancer cell.

11. The method of claim 10, wherein said cancer cell is selected from the group consisting of a brain cancer cell, a lung cancer cell, a breast cancer cell, a prostate cancer cell, and a colon cancer cell.

12. The method of claim 10, wherein said cancer cell is from a cancer cell line.

13. The method of claim 9, wherein the miRNA comprises the sequence set forth in SEQ ID NO: 52.

14. The method of claim 9, wherein the miRNA is miR-7.

15. The method of claim 9, wherein the miR-7 is the sequence set forth in SEQ ID NO: 48.

16. The method of claim 9, wherein the miRNA comprises a nucleic acid molecule having at least about 90% identity with the sequence set forth in SEQ ID NO: 48.

* * * * *

UNITED STATES PATENT AND TRADEMARK OFFICE
CERTIFICATE OF CORRECTION

PATENT NO. : 8,673,872 B2　　　　　　　　　　　　　　　　　　　　　Page 1 of 1
APPLICATION NO. : 12/310509
DATED : March 18, 2014
INVENTOR(S) : Leedman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 90

<210> SEQ ID NO 1
<211> LENGTH: 418
<212> TYPE: DNA
<213> ORGANISM: homo sapiens
```

<400> SEQUENCE: 1

```
tttcattgtc gctattgatt tttacttcaa tgggctcttc caacaaggaa gaagcttgct      60
ggtagcactt gctaccctga gttcatccag gcccaactgt gagcaaggag cacaagccac     120
aagtcttcca gaggatgctt gattccagtg gttctgcttc aaggcttcca ctgcaaaaca     180
ctaaagatcc aagaaggcct tcatggcccc agcaggccgg atcggtactg tatcaagtca     240
tggcaggtac agtaggataa gccactctgt cccttcctgg gcaaagaaga aacggagggg     300
atggaattct tccttagact tactttgta aaaatgtccc cacggtactt actccccact      360
gatggaccag tggtttccag tcatgagcgt tagactgact tgtttgtctt ccattcca       418
```

<210> SEQ ID NO 2
<211> LENGTH: 418
<212> TYPE: DNA
<213> ORGANISM: pan troglodytes

<400> SEQUENCE: 2

```
tttcattgtc gctattgatt tttacttcaa tgggctcttc caacaaggaa gaagcttgct      60
ggtagcactt gctaccctga gttcatccag gcccaactgt gagcaaggag cacaagccac     120
aagtcttcca gaggatgctt gattccagtg gttctgcttc aaggcttcca ctgcaaaaca     180
ctaaagatcc aagaaggcct tcatggcccc agcaggccgg atcggtactg tatcaagtca     240
tggcaggtac agtaggataa gccactctgt cccttcctgg gcaaagaaga aacggagggg     300
atggaattct tccttagact tactttgta aaaatgtccc cacggtactt actccccact      360
gatggaccag tggtttccag tcatgagcgt tagactgact tgtttgtctt ccattcca       418
```

<210> SEQ ID NO 3
<211> LENGTH: 418
<212> TYPE: DNA
<213> ORGANISM: pan troglodytes

<400> SEQUENCE: 3

```
tttcattgtc gctattgatt tttacttcaa tgggctcttc caacaaggaa gaagcttgct      60
ggtagcactt gctaccctga gttcatccag gcccaactgt gagcaaggag cacaagccac     120
aagtcttcca gaggatgctt gattccagtg gttctgcttc aaggcttcca ctgcaaaaca     180
ctaaagatcc aagaaggcct tcatggcccc agcaggccgg atcggtactg tatcaagtca     240
tggcaggtac agtaggataa gccactctgt cccttcctgg gcaaagaaga aacggagggg     300
atggaattct tccttagact tactttgta aaaatgtccc cacggtactt actccccact      360
gatggaccag tggtttccag tcatgagcgt tagactgact tgtttgtctt ccattcca       418
```

<210> SEQ ID NO 4
<211> LENGTH: 418
<212> TYPE: DNA
<213> ORGANISM: pan troglodytes

<400> SEQUENCE: 4

```
tttcattgtc gctattgatt tttacttcaa tgggctcttc caacaaggaa gaagcttgct      60
ggtagcactt gctaccctga gttcatccag gcccaactgt gagcaaggag cacaagccac     120
aagtcttcca gaggatgctt gattccagtg gttctgcttc aaggcttcca ctgcaaaaca     180
ctaaagatcc aagaaggcct tcatggcccc agcaggccgg atcggtactg tatcaagtca     240
tggcaggtac agtaggataa gccactctgt cccttcctgg gcaaagaaga aacggagggg     300
```

```
atggaattct tccttagact tacttttgta aaaatgtccc cacggtactt actccccact    360
gatggaccag tggtttccag tcatgagcgt tagactgact tgtttgtctt ccattcca      418
```

<210> SEQ ID NO 5
<211> LENGTH: 418
<212> TYPE: DNA
<213> ORGANISM: pan troglodytes

<400> SEQUENCE: 5

```
tttcattgtc gctattgatt tttacttcaa tgggctcttc caacaaggaa gaagcttgct     60
ggtagcactt gctaccctga gttcatccag gcccaactgt gagcaaggag cacaagccac    120
aagtcttcca gaggatgctt gattccagtg gttctgcttc aaggcttcca ctgcaaaaca    180
ctaaagatcc aagaaggcct tcatggcccc agcaggccgg atcggtactg tatcaagtca    240
tggcaggtac agtaggataa gccactctgt cccttcctgg gcaaagaaga aacggagggg    300
atggaattct tccttagact tacttttgta aaaatgtccc cacggtactt actccccact    360
gatggaccag tggtttccag tcatgagcgt tagactgact tgtttgtctt ccattcca      418
```

<210> SEQ ID NO 6
<211> LENGTH: 418
<212> TYPE: DNA
<213> ORGANISM: homo sapiens

<400> SEQUENCE: 6

```
tttcattgtc gctattgatt tttacttcaa tgggctcttc caacaaggaa gaagcttgct     60
ggtagcactt gctaccctga gttcatccag gcccaactgt gagcaaggag cacaagccac    120
aagtcttcca gaggatgctt gattccagtg gttctgcttc aaggcttcca ctgcaaaaca    180
ctaaagatcc aagaaggcct tcatggcccc agcaggccgg atcggtactg tatcaagtca    240
tggcaggtac agtaggataa gccactctgt cccttcctgg gcaaagaaga aacggagggg    300
atggaattct tccttagact tacttttgta aaaatgtccc cacggtactt actccccact    360
gatggaccag tggtttccag tcatgagcgt tagactgact tgtttgtctt ccattcca      418
```

<210> SEQ ID NO 7
<211> LENGTH: 418
<212> TYPE: DNA
<213> ORGANISM: homo sapiens

<400> SEQUENCE: 7

```
tttcattgtc gctattgatt tttacttcaa tgggctcttc caacaaggaa gaagcttgct     60
ggtagcactt gctaccctga gttcatccag gcccaactgt gagcaaggag cacaagccac    120
aagtcttcca gaggatgctt gattccagtg gttctgcttc aaggcttcca ctgcaaaaca    180
ctaaagatcc aagaaggcct tcatggcccc agcaggccgg atcggtactg tatcaagtca    240
tggcaggtac agtaggataa gccactctgt cccttcctgg gcaaagaaga aacggagggg    300
atggaattct tccttagact tacttttgta aaaatgtccc cacggtactt actccccact    360
gatggaccag tggtttccag tcatgagcgt tagactgact tgtttgtctt ccattcca      418
```

<210> SEQ ID NO 8
<211> LENGTH: 418
<212> TYPE: DNA
<213> ORGANISM: homo sapiens

```
<400> SEQUENCE: 8
tttcattgtc gctattgatt tttacttcaa tgggctcttc caacaaggaa gaagcttgct        60
ggtagcactt gctaccctga gttcatccag gcccaactgt gagcaaggag cacaagccac       120
aagtcttcca gaggatgctt gattccagtg gttctgcttc aaggcttcca ctgcaaaaca       180
ctaaagatcc aagaaggcct tcatggcccc agcaggccgg atcggtactg tatcaagtca       240
tggcaggtac agtaggataa gccactctgt cccttcctgg gcaaagaaga aacggagggg       300
atggaattct tccttagact tactttgta aaaatgtccc cacggtactt actccccact        360
gatggaccag tggtttccag tcatgagcgt tagactgact tgtttgtctt ccattcca         418

<210> SEQ ID NO 9
<211> LENGTH: 418
<212> TYPE: DNA
<213> ORGANISM: pan troglodytes

<400> SEQUENCE: 9
tttcattgtc gctattgatt tttacttcaa tgggctcttc caacaaggaa gaagcttgct        60
ggtagcactt gctaccctga gttcatccag gcccaactgt gagcaaggag cacaagccac       120
aagtcttcca gaggatgctt gattccagtg gttctgcttc aaggcttcca ctgcaaaaca       180
ctaaagatcc aagaaggcct tcatggcccc agcaggccgg atcggtactg tatcaagtca       240
tggcaggtac agtaggataa gccactctgt cccttcctgg gcaaagaaga aacggagggg       300
atggaattct tccttagact tactttgta aaaatgtccc cacggtactt actccccact        360
gatggaccag tggtttccag tcatgagcgt tagactgact tgtttgtctt ccattcca         418

<210> SEQ ID NO 10
<211> LENGTH: 417
<212> TYPE: DNA
<213> ORGANISM: homo sapiens

<400> SEQUENCE: 10
tttcattgtc gctattgatt tttacttcaa tgggctcttc caacaaggaa gaagcttgct        60
ggtagcactt gctaccctga gttcatccag gcccaactgt gagcaaggag cacaagccac       120
aagtcttcca gaggatgctt gattccagtg gttctgcttc aaggcttcca ctgcaaaaca       180
ctaaagatcc aagaaggcct tcatggcccc agcaggccgg atcggtactg tatcaagtca       240
tggcaggtac agtaggataa gccactctgt cccttcctgg gcaaagaaga aacggagggg       300
atgaattctt ccttagactt acttttgtaa aaatgtcccc acggtactta ctccccactg       360
atggaccagt ggtttccagt catgagcgtt agactgactt gtttgtcttc cattcca          417

<210> SEQ ID NO 11
<211> LENGTH: 417
<212> TYPE: DNA
<213> ORGANISM: HOMO SAPIENS

<400> SEQUENCE: 11
tttcattgtc gctattgatt tttacttcaa tgggctcttc caacaaggaa gaagcttgct        60
ggtagcactt gctaccctga gttcatccag gcccaactgt gagcaaggag cacaagccac       120
aagtcttcca gaggatgctt gattccagtg gttctgcttc aaggcttcca ctgcaaaaca       180
ctaaagatcc aagaaggcct tcatggcccc agcaggccgg atcggtactg tatcaagtca       240
tggcaggtac agtaggataa gccactctgt cccttcctgg gcaaagaaga aacggagggg       300
```

```
atgaattctt ccttagactt acttttgtaa aaatgtcccc acggtactta ctccccactg    360
atggaccagt ggtttccagt catgagcgtt agactgactt gtttgtcttc cattcca       417

<210> SEQ ID NO 12
<211> LENGTH: 399
<212> TYPE: DNA
<213> ORGANISM: sus scrofa

<400> SEQUENCE: 12
gtcgtcattg attttgcttt taacgggctt ttccaacgag gaagaagctc acttgtagca    60
cttgggccgc agagtccacc cagatacggg accagcccgg gccagccttc cactaacact   120
tgattccact ggctctgctc ggaggctctt ccactgcaag gcagttgaaa accagctagt   180
tctccgtgtc ccaggcaggc ccgattggta ctctgtcaaa tcatgtcagg tgcaagagga   240
taagccactt tgaacccttc ctgggcaggg gagaaaagga gggtagaatt cctcctcaga   300
cttactttta tccaaatatc tccacggtac ttaccctcca ttgagtgacc agtgttttct   360
gattatatgt gttggattta cttgtttatt ttccattcc                          399

<210> SEQ ID NO 13
<211> LENGTH: 397
<212> TYPE: DNA
<213> ORGANISM: bos taurus

<400> SEQUENCE: 13
ttttactttt aatgagcttt tctaataagg aaaaagcttg ctcatagcac ctgtggtact    60
gagttgaccc aggcccaact gtgactgaga cgcacggacc agccttccag ccaacacgtg   120
attccattgg ctctgcttgg agactcctcc actgcaagtc agttgaataa ccagccagtc   180
ctctgagttc tcagcaggcc acattggtac tatctcagat caaggcaggt acaagacaat   240
aagccacttt gaactcttcc tgagcaagga agaaacagag ggagtagaat tcttcctcag   300
acttacttgt atatagatgt ctccatggta cttttctctcc tttgggtgac cagtgtattt   360
taattataag tattagactt gtttattttc cattcca                            397

<210> SEQ ID NO 14
<211> LENGTH: 213
<212> TYPE: DNA
<213> ORGANISM: mus musculus

<400> SEQUENCE: 14
ttggttccac cagctctgca tcaagacact tccgtggcaa gacaactaaa tgtataagaa    60
gtccatggat gccctgagca ggccacactt gtacagcatt aaaccatggc agatacaata   120
ggataagcca ctttgttact tactgggggct gggagaagag gaatgacggg gtagaatttt   180
ccctcagacg tactttttat ataaatatgt ccc                                213

<210> SEQ ID NO 15
<211> LENGTH: 213
<212> TYPE: DNA
<213> ORGANISM: mus musculus

<400> SEQUENCE: 15
ttggttccac cagctctgca tcaagacact tccgtggcaa gacaactaaa tgtataagaa    60
gtccatggat gccctgagca ggccacactt gtacagcatt aaaccatggc agatacaata   120
ggataagcca ctttgttact tactgggggct gggagaagag gaatgacggg gtagaatttt   180
ccctcagacg tactttttat ataaatatgt ccc                                213
```

<210> SEQ ID NO 16
<211> LENGTH: 213
<212> TYPE: DNA
<213> ORGANISM: mus musculus

<400> SEQUENCE: 16
ttggttccac cagctctgca tcaagacact tccgtggcaa gacaactaaa tgtataagaa    60
gtccatggat gccctgagca ggccacactt gtacagcatt aaaccatggc agatacaata   120
ggataagcca ctttgttact tactggggct gggagaagag gaatgacggg gtagaatttt   180
ccctcagacg tacttttat ataaatatgt ccc                                 213

<210> SEQ ID NO 17
<211> LENGTH: 213
<212> TYPE: DNA
<213> ORGANISM: MUS MUSCULUS

<400> SEQUENCE: 17
ttggttccac cagctctgca tcaagacact tccgtggcaa gacaactaaa tgtataagaa    60
gtccatggat gccctgagca ggccacactt gtacagcatt aaaccatggc agatacaata   120
ggataagcca ctttgttact tactggggct gggagaagag gaatgacggg gtagaatttt   180
ccctcagacg tacttttat ataaatatgt ccc                                 213

<210> SEQ ID NO 18
<211> LENGTH: 213
<212> TYPE: DNA
<213> ORGANISM: mus musculus

<400> SEQUENCE: 18
ttggttccac cagctctgca tcaagacact tccgtggcaa gacaactaaa tgtataagaa    60
gtccatggat gccctgagca ggccacactt gtacagcatt aaaccatggc agatacaata   120
ggataagcca ctttgttact tactggggct gggagaagag gaatgacggg gtagaatttt   180
ccctcagacg tacttttat ataaatatgt ccc                                 213

<210> SEQ ID NO 19
<211> LENGTH: 213
<212> TYPE: DNA
<213> ORGANISM: mus musculus

<400> SEQUENCE: 19
ttggttccac cagctctgca tcaagacact tccgtggcaa gacaactaaa tgtataagaa    60
gtccatggat gccctgagca ggccacactt gtacagcatt aaaccatggc agatacaata   120
ggataagcca ctttgttact tactggggct gggagaagag gaatgacggg gtagaatttt   180
ccctcagacg tacttttat ataaatatgt ccc                                 213

<210> SEQ ID NO 20
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 20
atttttactt caatgggctc ttcca                                           25

<210> SEQ ID NO 21
<211> LENGTH: 25
<212> TYPE: DNA
<213> ORGANISM: Artificial Sequence

```
<220> FEATURE:
<223> OTHER INFORMATION: Synthetic Oligonucleotide

<400> SEQUENCE: 21
attttatttc tcgtgggctt ttcca                                          25

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
atttgattga tgcactcttg ta                                             22

<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 23
atttgattca tgcactcttc ca                                             22

<210> SEQ ID NO 24
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 24
aggagcacaa gccacaagtc ttcca                                          25

<210> SEQ ID NO 25
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 25
agaagcaagg gtcagagtct tcca                                           24

<210> SEQ ID NO 26
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 26
gttagactga cttgtttgtc ttcca                                          25

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
atcggaccta attttcca                                                  18
```

```
<210> SEQ ID NO 28
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 28
attagacttc cttctatgtt ttctg                                              25

<210> SEQ ID NO 29
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 29
attagactac cttttatgtt ttctg                                              25

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 30
caacaaaatc actagtcttc ca                                                 22

<210> SEQ ID NO 31
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 31 ctcttcca                                                                  8

<210> SEQ ID NO 32
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 32 cttttcca                                                                  8

<210> SEQ ID NO 33
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 33 ctcttgta                                                                  8

<210> SEQ ID NO 34
<211> LENGTH: 8
<212> TYPE: DNA
<213> ORGANISM: Artificial Sequence
<220> FEATURE:
<223> OTHER INFORMATION: Synthetic Oligonucleotide
```

```
<400> SEQUENCE: 34 gtcttcca                                                              8

<210> SEQ ID NO 35
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 35 gtcttcca                                                              8

<210> SEQ ID NO 36
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 36 gttttctg                                                              8

<210> SEQ ID NO 37
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 37
uggaagagcc cauugaagua aaaau                                          25

<210> SEQ ID NO 38
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 38
uggaaaagcc cacgagaaau aaaau                                          25

<210> SEQ ID NO 39
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 39
uacaagagug caucaaucaa au                                             22

<210> SEQ ID NO 40
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 40
uggaagagug caugaaucaa au                                             22
```

```
<210> SEQ ID NO 41
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 41
uggaagacuu guggcuugug cuccu                                    25

<210> SEQ ID NO 42
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 42
uggaagacuc ugacccuugc uucu                                     24

<210> SEQ ID NO 43
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 43
uggaagacuc ugacccuugc uucu                                     24

<210> SEQ ID NO 44
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 44
uggaagacaa acacgucagu cuaag                                    25

<210> SEQ ID NO 45
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 45
uggaaaauua gguccgau                                            18

<210> SEQ ID NO 46
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 46
cagaaaacau agaaggaagu cuaau                                    25

<210> SEQ ID NO 47
<211> LENGTH: 25
<212> TYPE: RNA
<213> ORGANISM: Artificial Sequence
<220> FEATURE:
<223> OTHER INFORMATION: Synthetic Oligonucleotide
```

-continued

<400> SEQUENCE: 47
cagaaaacau aaaagguagu cuaau     25

<210> SEQ ID NO 48
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 48
uggaagacua gugauuuugu ug     22

<210> SEQ ID NO 49
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 49 uggaagag     8

<210> SEQ ID NO 50
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 50 uggaaaag     8

<210> SEQ ID NO 51
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 51 uacaagag     8

<210> SEQ ID NO 52
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 52 uggaagac     8

<210> SEQ ID NO 53
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 53 uggaagac     8

```
<210> SEQ ID NO 54
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 54 cagaaaac                                                                 8

<210> SEQ ID NO 55
<211> LENGTH: 22
<212> TYPE: DNA
<213> ORGANISM: HOMO SAPIENS

<400> SEQUENCE: 55
caacaaaatc actagtcttc ca                                                22

<210> SEQ ID NO 56
<211> LENGTH: 22
<212> TYPE: DNA
<213> ORGANISM: HOMO SAPIENS

<400> SEQUENCE: 56
tggaagacta gtgattttgt tg                                                22

<210> SEQ ID NO 57
<211> LENGTH: 20
<212> TYPE: DNA
<213> ORGANISM: HOMO SAPIENS

<400> SEQUENCE: 57
caccgactag ccaggaagta                                                   20

<210> SEQ ID NO 58
<211> LENGTH: 31
<212> TYPE: DNA
<213> ORGANISM: HOMO SAPIENS

<400> SEQUENCE: 58
aagcttcttc cttgttggaa gagcccattg a                                      31

<210> SEQ ID NO 59
<211> LENGTH: 20
<212> TYPE: DNA
<213> ORGANISM: HOMO SAPIENS

<400> SEQUENCE: 59
gccaacacag tgctgtctgg                                                   20

<210> SEQ ID NO 60
<211> LENGTH: 20
<212> TYPE: DNA
<213> ORGANISM: HOMO SAPIENS

<400> SEQUENCE: 60
tactcctgct tgctgatcca                                                   20

<210> SEQ ID NO 61
<211> LENGTH: 21
<212> TYPE: DNA
<213> ORGANISM: HOMO SAPIENS

<400> SEQUENCE: 61
gcactgtagc accaaagtac c                                                 21
```

```
<210> SEQ ID NO 62
<211> LENGTH: 23
<212> TYPE: DNA
<213> ORGANISM: HOMO SAPIENS

<400> SEQUENCE: 62
ctgggactcc actatcacca ata                                              23

<210> SEQ ID NO 63
<211> LENGTH: 19
<212> TYPE: DNA
<213> ORGANISM: HOMO SAPIENS

<400> SEQUENCE: 63
atggggaagg tgaaggtcg                                                   19

<210> SEQ ID NO 64
<211> LENGTH: 22
<212> TYPE: DNA
<213> ORGANISM: HOMO SAPIENS

<400> SEQUENCE: 64
ggggtcattg atggcaacaa ta                                               22

<210> SEQ ID NO 65
<211> LENGTH: 25
<212> TYPE: RNA
<213> ORGANISM: Homo sapiens

<400> SEQUENCE: 65
auuuuuacuu caaugggcuc uucca                                            25

<210> SEQ ID NO 66
<211> LENGTH: 25
<212> TYPE: RNA
<213> ORGANISM: Pan troglodytes

<400> SEQUENCE: 66
auuuuuacuu caaugggcuc uucca                                            25

<210> SEQ ID NO 67
<211> LENGTH: 25
<212> TYPE: RNA
<213> ORGANISM: Canis familiaris

<400> SEQUENCE: 67
auuuuauuuc ucgugggcuu uucca                                            25

<210> SEQ ID NO 68
<211> LENGTH: 22
<212> TYPE: RNA
<213> ORGANISM: Mus musculus

<400> SEQUENCE: 68
auuugauuga ugcacucuug ua                                               22

<210> SEQ ID NO 69
<211> LENGTH: 22
<212> TYPE: RNA
<213> ORGANISM: Rattus norvegicus

<400> SEQUENCE: 69
auuugauuca ugcacucuuc ca                                               22
```

```
<210> SEQ ID NO 70
<211> LENGTH: 25
<212> TYPE: RNA
<213> ORGANISM: Homo sapiens

<400> SEQUENCE: 70
aggagcacaa gccacaaguc uucca                                              25

<210> SEQ ID NO 71
<211> LENGTH: 25
<212> TYPE: RNA
<213> ORGANISM: Pan troglodytes

<400> SEQUENCE: 71
aggagcacaa gccacaaguc uucca                                              25

<210> SEQ ID NO 72
<211> LENGTH: 24
<212> TYPE: RNA
<213> ORGANISM: Canis familiaris

<400> SEQUENCE: 72
agaagcaagg gucagagucu ucca                                               24

<210> SEQ ID NO 73
<211> LENGTH: 5
<212> TYPE: RNA
<213> ORGANISM: Mus musculus

<400> SEQUENCE: 73 gacag                                                                     5

<210> SEQ ID NO 74
<211> LENGTH: 5
<212> TYPE: RNA
<213> ORGANISM: Rattus norvegicus

<400> SEQUENCE: 74 gacag                                                                     5

<210> SEQ ID NO 75
<211> LENGTH: 25
<212> TYPE: RNA
<213> ORGANISM: Homo sapiens

<400> SEQUENCE: 75
guuagacuga cuuguuuguc uucca                                              25

<210> SEQ ID NO 76
<211> LENGTH: 25
<212> TYPE: RNA
<213> ORGANISM: Pan troglodytes

<400> SEQUENCE: 76
guuagacuga cuuguuuguc uucca                                              25

<210> SEQ ID NO 77
<211> LENGTH: 18
<212> TYPE: RNA
<213> ORGANISM: Canis familiaris

<400> SEQUENCE: 77
aucggaccua auuuucca                                                      18
```

```
<210> SEQ ID NO 78
<211> LENGTH: 25
<212> TYPE: RNA
<213> ORGANISM: Mus musculus

<400> SEQUENCE: 78
auuagacuuc cuucuauguu uucug                                          25

<210> SEQ ID NO 79
<211> LENGTH: 25
<212> TYPE: RNA
<213> ORGANISM: Rattus norvegicus

<400> SEQUENCE: 79
auuagacuac cuuuuauguu uucug                                          25

<210> SEQ ID NO 80
<211> LENGTH: 22
<212> TYPE: RNA
<213> ORGANISM: Homo sapiens

<400> SEQUENCE: 80
uggaagacua gugauuuugu ug                                             22

<210> SEQ ID NO 81
<211> LENGTH: 26
<212> TYPE: RNA
<213> ORGANISM: Homo sapiens

<400> SEQUENCE: 81
gauuuuuacu ucaaugggcu cuucca                                         26

<210> SEQ ID NO 82
<211> LENGTH: 26
<212> TYPE: RNA
<213> ORGANISM: Artificial sequence
<220> FEATURE:
<223> OTHER INFORMATION: Syntheic oligonucleotide

<400> SEQUENCE: 82
gauuuuuacu ucaaugggca cguaca                                         26

<210> SEQ ID NO 83
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 83
aggagcacaa gccacaaguc uucca                                          25

<210> SEQ ID NO 84
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 84
aggagcacaa gccacaagcc cuuca                                          25

<210> SEQ ID NO 85
<211> LENGTH: 24
<212> TYPE: RNA
<213> ORGANISM: Artificial Sequence
```

-continued

```
<220> FEATURE:
<223> OTHER INFORMATION: Synthetic oligonucleotide

<400> SEQUENCE: 85
uuagacugac uuguuugucu ucca                                              24

<210> SEQ ID NO 86
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 86
uuagacugac uuguuugccc uuca                                              24

<210> SEQ ID NO 87
<211> LENGTH: 23
<212> TYPE: RNA
<213> ORGANISM: Homo sapiens

<400> SEQUENCE: 87
cccucucagg gagcagucuu cca                                               23

<210> SEQ ID NO 88
<211> LENGTH: 22
<212> TYPE: RNA
<213> ORGANISM: Homo sapiens

<400> SEQUENCE: 88
ucaugcugaa uuuugucuuc ca                                                22

<210> SEQ ID NO 89
<211> LENGTH: 23
<212> TYPE: RNA
<213> ORGANISM: Artificial
<220> FEATURE:
<223> OTHER INFORMATION: Synthetic oligonucleotide

<400> SEQUENCE: 89
cccucucagg gagcauuauc cua                                               23

<210> SEQ ID NO 90
<211> LENGTH: 22
<212> TYPE: RNA
<213> ORGANISM: Artificial Sequence
<220> FEATURE:
<223> OTHER INFORMATION: Synthetic oligonicleotide

<400> SEQUENCE: 90
ucaugcugaa uuuuuuaucc ua                                                22
```